United States Patent [19]
Datta et al.

[11] Patent Number: 5,722,968
[45] Date of Patent: Mar. 3, 1998

[54] ABSORBENT ARTICLE FASTENING SYSTEM

[75] Inventors: Paul Joseph Datta; Bernhardt Edward Kressner, both of Appleton, Wis.

[73] Assignee: Kimberly-Clark Worldwide, Inc., Neenah, Wis.

[21] Appl. No.: 790,088

[22] Filed: Jan. 29, 1997

Related U.S. Application Data

[63] Continuation of Ser. No. 579,394, Dec. 27, 1995, abandoned.

[51] Int. Cl.$^6$ .................................................... A61F 13/15
[52] U.S. Cl. ........................ 604/391; 604/392; 604/398; 24/450
[58] Field of Search ........................ 604/389–393, 604/398, 385.1; 24/445, 451, 442, 306

[56] References Cited

U.S. PATENT DOCUMENTS

| | | | |
|---|---|---|---|
| 3,574,019 | 4/1971 | Girard | 156/66 |
| 3,618,608 | 11/1971 | Brink | 128/287 |
| 3,688,348 | 9/1972 | Klotz et al. | 24/16 |
| 3,708,382 | 1/1973 | Erb | 161/48 |
| 3,717,908 | 2/1973 | Perina | 26/204 |
| 3,747,171 | 7/1973 | Montague, Jr. | 24/442 |
| 4,047,651 | 9/1977 | McMullen | 224/4 D |
| 4,058,853 | 11/1977 | Boxer et al. | 2/239 |
| 4,114,297 | 9/1978 | Famolare, Jr. | 36/50 |
| 4,216,257 | 8/1980 | Schams et al. | 428/93 |
| 4,291,439 | 9/1981 | Riti | 24/119 |
| 4,294,238 | 10/1981 | Woodford | 128/80 G |
| 4,315,508 | 2/1982 | Bolick | 128/289 |
| 4,388,075 | 6/1983 | Mesek et al. | 604/385 |
| 4,416,951 | 11/1983 | Mesnel | 428/586 |
| 4,488,316 | 12/1984 | Mosca | 2/171 |
| 4,500,316 | 2/1985 | Damico | 604/389 |
| 4,596,540 | 6/1986 | F'Geppert | 474/253 |
| 4,617,022 | 10/1986 | Pigneul et al. | 604/391 |
| 4,662,037 | 5/1987 | Provost et al. | 24/447 |
| 4,699,823 | 10/1987 | Kellenberger et al. | 428/219 |
| 4,728,553 | 3/1988 | Daniels | 423/100 |
| 4,770,917 | 9/1988 | Tochacek et al. | 428/95 |
| 4,780,936 | 11/1988 | Brecher | 24/119 |
| 4,831,997 | 5/1989 | Greene | 124/35 A |
| 4,861,322 | 8/1989 | Reddick | 474/254 |
| 4,862,563 | 9/1989 | Flynn | 24/442 |
| 4,870,725 | 10/1989 | Dubowik | 24/442 |
| 4,887,339 | 12/1989 | Bellanger | 24/575 |
| 4,894,060 | 1/1990 | Nestegard | 604/391 |

(List continued on next page.)

FOREIGN PATENT DOCUMENTS

| | | |
|---|---|---|
| 0 617 941 A1 | 10/1994 | European Pat. Off. |
| 92 13 186 | 4/1993 | Germany |
| 9213186 U1 | 4/1993 | Germany |
| WO 85/03205 A1 | 8/1985 | WIPO |
| WO 86/02263 A1 | 4/1986 | WIPO |
| 9303644 | 3/1993 | WIPO |
| 9505140 | 2/1995 | WIPO |

*Primary Examiner*—John G. Weiss
*Assistant Examiner*—Ki Yong O
*Attorney, Agent, or Firm*—Thomas M. Gage; Patricia A. Charlier

[57] ABSTRACT

An absorbent article includes a fastening system that is adapted to resist pop-offs caused by clothing being applied or removed over the absorbent article. The fastening system includes an interlocking fastening component with a resilient backing structure and a plurality of engaging elements projecting from a first major surface of the backing structure. The first major surface has a concave configuration in the direction of a primary meridian, a generally perpendicular secondary meridian, or both the primary and secondary meridians. The concavity of the interlocking fastening component is characterized in terms of a bending index of the first major surface or an amount of elevation of a central portion of the first major surface.

18 Claims, 6 Drawing Sheets

U.S. PATENT DOCUMENTS

| | | | |
|---|---|---|---|
| 4,931,343 | 6/1990 | Becker et al. | 428/95 |
| 4,938,754 | 7/1990 | Mesek | 604/385.2 |
| 4,941,237 | 7/1990 | Hovis | 24/304 |
| 4,964,860 | 10/1990 | Gipson et al. | 604/391 |
| 4,973,326 | 11/1990 | Wood et al. | 604/391 |
| 4,999,853 | 3/1991 | Tanner | 2/321 |
| 5,019,073 | 5/1991 | Roessler et al. | 604/391 |
| 5,049,145 | 9/1991 | Flug | 604/391 |
| 5,053,028 | 10/1991 | Zoia et al. | 604/391 |
| 5,077,870 | 1/1992 | Melbye et al. | 24/452 |
| 5,147,343 | 9/1992 | Kellenberger | 604/368 |
| 5,227,107 | 7/1993 | Dickenson et al. | 264/113 |
| 5,304,162 | 4/1994 | Kuen | 604/391 |
| 5,325,569 | 7/1994 | Goulait et al. | 604/391 |
| 5,374,262 | 12/1994 | Keuhn, Jr. et al. | 604/392 |
| 5,386,595 | 2/1995 | Kuen et al. | 2/400 |
| 5,476,702 | 12/1995 | Datta et al. | 428/99 |

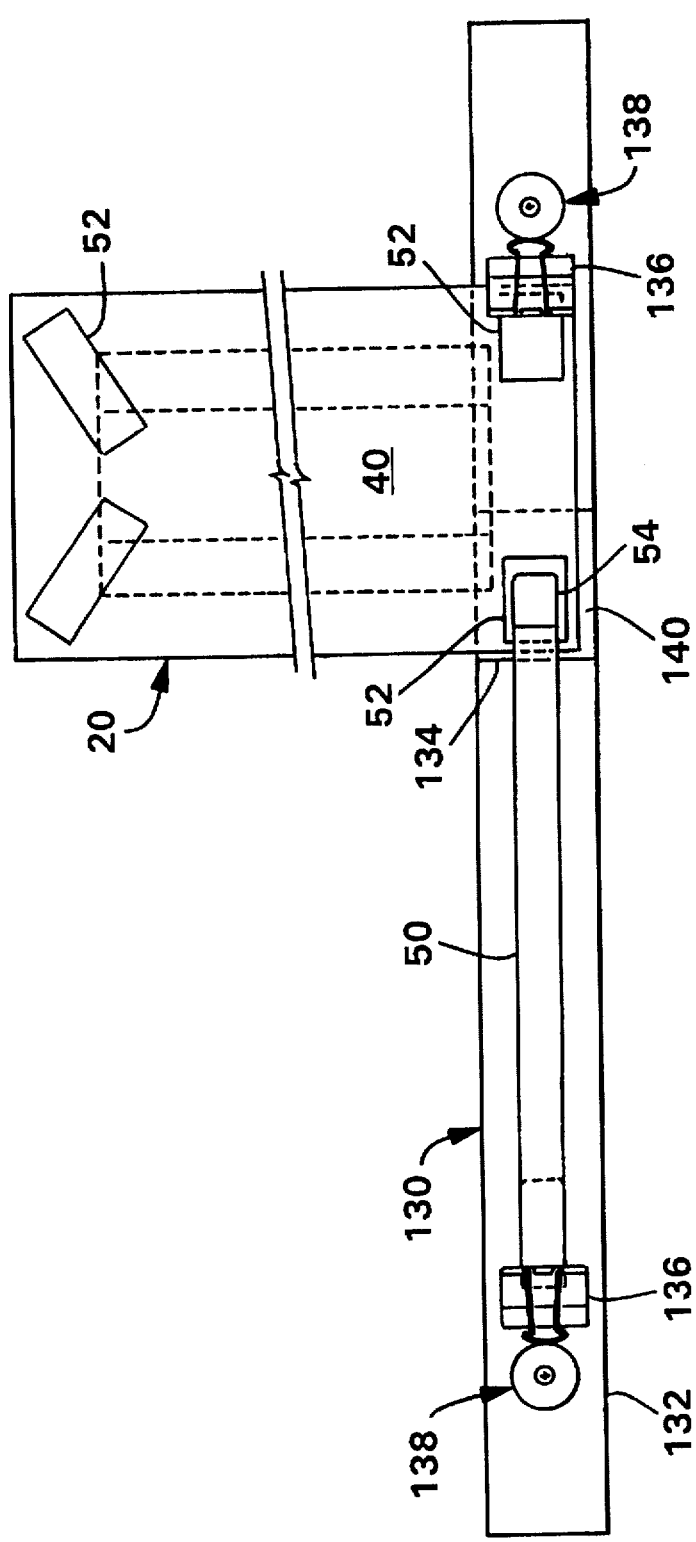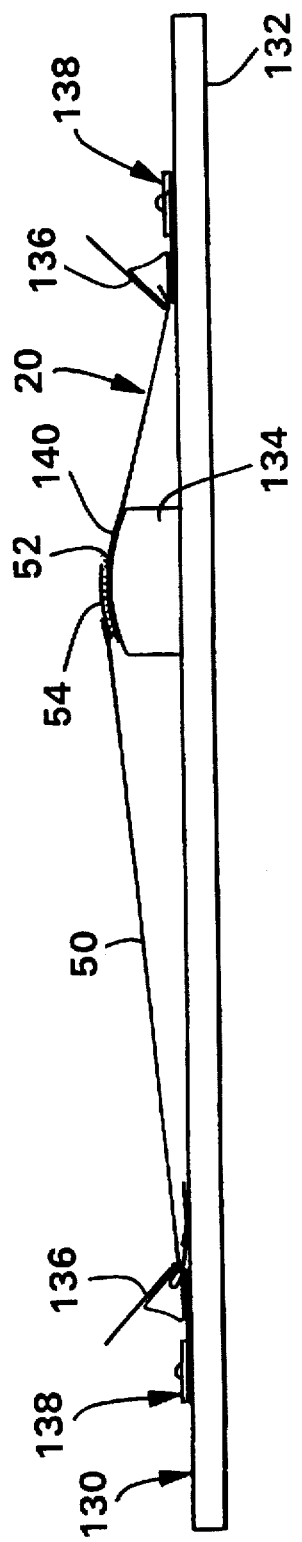
FIG. 10
FIG. 11

ABSORBENT ARTICLE FASTENING SYSTEM

This application is a continuation of application Ser. No. 08/579,394 entitled "ABSORBENT ARTICLE FASTENING SYSTEM" and filed in the U.S. Patent and Trademark Office on Dec. 27, 1995 now abandoned. The entirety of this application is hereby incorporated by reference.

BACKGROUND OF THE INVENTION

The present invention relates to an absorbent article having an improved fastening system and a method of making such an absorbent article. More particularly, the invention pertains to an absorbent article that is maintained in place about a wearer by a fastening system that is adapted to resist pop-offs.

Absorbent articles such as adult incontinence products, training pants, diapers and sanitary napkins have been constructed with a wide variety of unique fastening systems. Among the most commonly employed fastening systems are adhesive tape fasteners, garment attachment adhesives, straps with buttons, stretchable side panels, and interlocking fastening components. The type of fastening system is selected to maintain the particular product form in proper position until removed by the wearer or caregiver.

Over the last several years, fastening systems using interlocking fastening components have become more prevalent on commercial absorbent articles. The term interlocking fastening component refers to a material that refastenably connects to a mating material through the use of engaging elements so that the mating materials resist disengagement in a shear mode and allow disengagement in a peel mode. Hook-and-loop fasteners are the most widespread example of interlocking fastening components. The recent enthusiasm for fastening systems using interlocking fastening components is attributable in part to heightened consumer acceptance of interlocking fastening components, as well as improved performance and decreased cost of such materials.

Despite this increased popularity of absorbent articles that incorporate fastening systems with interlocking fastening components, these fasteners remain subject to failures during use. Fastener failures may include such undesired events as disassembly of the fastener components, non-refastenability, or the like. One particularly significant form of failure for fasteners with interlocking fastening components is a pop-off, which refers to the unintentional disengagement of the interlocking fastening components from one another during use of the absorbent article. Needless to say, this is particularly undesirable for the wearer given the nature of the product.

To date, there have been many attempts to reduce the frequency of pop-offs for fastening systems with interlocking fastening components. These efforts have focused on the engaging elements of the interlocking fastening components, and have resulted in an astounding variety in the size, shape and arrangement of the engaging elements. Despite these past attempts to improve performance, however, absorbent articles that incorporate fastening systems with interlocking fastening components continue to experience an unacceptably high level of pop-offs.

Therefore, what is lacking and needed in the art is an absorbent article that is maintained in place about the wearer by a fastening system with interlocking fastening components that are adapted to resist pop-offs.

SUMMARY OF THE INVENTION

In response to the discussed deficiencies in the prior art, a new absorbent article has been developed. The absorbent article utilizes a fastening system with interlocking fastening components and provides improved resistance to pop-offs.

In one aspect, the present invention concerns the absorbent article including a garment and at least one strap member for securing the garment about the wearer. The garment has a first waist region, a second waist region, and a crotch region positioned between and interconnecting the first and second waist regions. A first interlocking fastening component is disposed in the first waist region of the garment. The strap member has opposite first and second end portions and includes a second interlocking fastening component bonded to the first end portion. The second interlocking fastening component is adapted for refastenable attachment to the first interlocking fastening component. The second interlocking fastening component includes a backing structure formed of a resilient material and having a concave first major surface with a bending index of at least about 0.3 inch$^{-1}$. A plurality of engaging elements project from the first major surface. The absorbent article also includes means for attaching the second end portion of the strap member to the second waist region.

In another aspect, the present invention concerns an absorbent article including a garment with a first waist region, a second waist region, and a crotch region positioned between and interconnecting the first and second waist regions. The garment has a first interlocking fastening component disposed in the first waist region. The absorbent article also includes at least one strap member for securing the garment about a wearer. The strap member has opposite first and second end portions with a second interlocking fastening component bonded to the first end portion. The second interlocking fastening component is adapted for refastenable attachment to the first interlocking fastening component. The second interlocking fastening component includes a backing structure formed of a resilient material and having a concave first major surface. A central portion of the first major surface is elevated by at least about 1.0 millimeter from a plane containing opposite peripheral points of the first major surface. A plurality of engaging elements project from the first major surface. The absorbent article also includes means for attaching the second end portion of the strap member to the second waist region.

In still another aspect, the present invention concerns an absorbent garment with a first waist region, a second waist region, and a crotch region positioned between and interconnecting the first and second waist regions. A first interlocking fastening component is disposed in the first waist region of the garment, and a second interlocking fastening component is disposed in the second waist region of the garment. The second interlocking fastening component, which is adapted for refastenable attachment to the first interlocking fastening component, includes a backing structure formed of a resilient material. The backing structure has a concave first major surface with a bending index of at least about 0.3 inch$^{-1}$, and a plurality of engaging elements project from the first major surface.

In a further aspect, the present invention concerns an absorbent garment having a first waist region, a second waist region, and a crotch region positioned between and interconnecting the first and second waist regions. The garment includes a first interlocking fastening component disposed in the first waist region, and a second interlocking fastening component disposed in the second waist region. The second interlocking fastening component is adapted for refastenable attachment to the first interlocking fastening component. The second interlocking fastening component includes a backing structure formed of a resilient material and having a concave first major surface. The first major surface has a central portion that is elevated by at least about 1.0 millimeter from a plane containing opposite peripheral points. A plurality of engaging elements project from the first major surface of the backing structure.

The absorbent articles may be in the form of adult incontinence products, training pants, diapers, sanitary napkins, or the like. Typically, the absorbent articles include a moisture barrier, an absorbent assembly disposed on the moisture barrier, and a bodyside liner bonded to the moisture boarder and sandwiching the absorbent assembly therebetween. Such absorbent articles are generally positioned in the crotch area and worn beneath underpants or other clothing.

For reasons of comfort and performance, the absorbent articles are generally constructed of flexible components so that they conform to the body of the wearer. Additionally, the first interlocking fastening component of the fastening system, which either forms an integral part of the garment or is a separate element attached to the garment, desirably comprises a generally flexible material. Consequently, the first interlocking fastening component tends to conform to the shape of the wearer and enhance comfort. In contrast, however, the second interlocking fastening component is desirably formed of a stiffer, resilient material so that the wearer or caregiver can easily grasp the second interlocking fastening component to disengage the fastening system. The term resilient refers to the property of the backing structure that enables it to resume its curved configuration after being bent as a result of disengagement of the mating interlocking materials. Thus, the resiliency of the second interlocking fastening component also minimizes the likelihood that the fastening component will become deformed, in which case the fastening component edges and/or engaging elements are exposed and tend to snag on clothing or other materials.

While the absorbent article is worn, the wearer or caregiver may apply or remove underpants or other clothing over the product. For example, clothing may be pulled over the absorbent article when initially putting on the product, changing clothes, going to the bathroom, checking or adjusting the product, or removing the product. Applicants have discovered that failure of the garment fastening system due to a pop-off of an interlocking fastening component is significantly more likely to result when the wearer is changing or adjusting clothing for these purposes than when the wearer is involved in activities such as walking, running, sleeping or sitting. Applicants theorize that the movement of clothing over the resilient interlocking fastening components greatly increases the likelihood of pop-offs. In particular, elastic waistbands included in underpants, pantyhose, or other clothing tend to catch on the edges and corners of resilient interlocking fastening components and cause pop-offs.

Applicants have discovered that absorbent articles including an interlocking fastening component having a resilient, concave backing structure are particularly well suited to maintain proper attachment of the fastening system when clothing is raised or lowered over the article. The edges and corners of the resilient, contoured interlocking fastening components do not project tangentially away from the body of the wearer as is the case with conventional flat interlocking fastening components. Applicants believe that the edges and corners of the contoured interlocking fastening components penetrate deeply into the mating interlocking materials. This deep penetration ensures that clothing or other materials passing over the garment fastening system are less likely to snag on protruding edges and corners. This is thought to be a particularly significant problem for small individuals, where the angles of curvature of the body may be greater than for less slim individuals.

The concavity of the interlocking fastening component may be characterized in terms of a bending index of the fastening component. The bending index is determined from the radius of curvature of the surface of the fastening component that includes the engaging elements. Specifically, the major surface including the engaging elements desirably has a bending index of at least 0.3 inch$^{-1}$, and more particularly at least about 0.5 inch$^{-1}$. For example, the bending index may be from 0.3 to about 1.1 inch$^{-1}$, and more particularly from about 0.5 to about 1.1 inch$^{-1}$. This concavity may be in the direction of either the primary meridian or the secondary meridian of the interlocking fastening component. In particular embodiments, the major surface including the engaging elements may have a concave configuration in the direction of both the primary and secondary meridians, in which case the fastening component is said to be three-dimensionally concave. By way of illustration, the major surface including the engaging elements may have a bending index in the direction of the primary meridian of at least about 0.6 inch$^{-1}$ and a bending index in the direction of the secondary meridian of at least about 1 inch$^{-1}$.

The concavity of the interlocking fastening component may also be characterized by the amount of elevation of a central portion of the fastening component. The elevation of the central portion of the interlocking fastening component is determined in relation to selected peripheral points on the fastening component. The peripheral points are located either longitudinally or transversely outward of the a selected central, intermediate point. The opposite peripheral points may correspond to the opposite edges of the interlocking fastening component or to points disposed between the central, intermediate point and the opposite edges. The major surface of the fastening component that includes the engaging elements desirably has a central portion that is elevated by at least about 1.0 millimeter, and more particularly at least about 1.5 millimeters, from a plane containing the peripheral points. By way of illustration, the central portion may be elevated by about 1.0 to about 2.0 millimeters, such as about 1.5 to about 2.0 millimeters, from a plane containing the opposite edges of the fastening component.

In particular aspects of the present invention the resilient backing structure of the curved interlocking fastening component is adapted to retain a concave shape after 15 attachment and detachment cycles of the first and second interlocking fastening components. As a result, the improved performance of the fastening system is sustained over multiple attachment and detachment cycles. This feature is particularly desirable for adult incontinence products, because such products commonly include a single set of elastic attachment straps for use with 15 to 20 or more garments. Because the resilient interlocking fastening components are desirably incorporated on the elastic attachment straps, the resilient interlocking fastening components should maintain their curvature in order to remain effective after use with several garments.

The ability of the resilient interlocking fastening component to retain a concave configuration can be enhanced by controlling the construction of the backing structure. The backing structure of the concave interlocking fastening component is desirably formed of a material that has sufficient memory characteristics that the backing structure will return to a concave configuration after repeated engagement and disengagement cycles with a complementary fastening component. In particular embodiments, the backing structure has a composition of nylon or polypropylene, a thickness of about 0.1 to about 0.5 millimeters, and a Gurley stiffness of about 250 to about 3000 milligrams. The present invention provides for the production of an absorbent article with a fastener that reduces pop-offs. In one aspect, the invention concerns a method of forming an absorbent article including the following steps: (1) providing a garment having a first waist region, a second waist region, and a crotch region positioned between and interconnecting the first and second waist regions; (2) bonding a first interlocking fastening component to the first waist region; (3) providing at least one strap member having opposite first and second end portions; (4) providing a second interlocking fastening component adapted for refastenable attachment to the first interlocking fastening component, the second interlocking fastening component comprising a backing structure formed of a resilient material and having a first major surface with a plurality of engaging elements projecting from the first major surface; (5) forming the first major surface with a concave configuration and a bending index of at least about 0.3 inch$^{-1}$; (6) bonding the second interlocking fastening component to the first end portion; and (7) providing the second end portion with means for attaching the second end portion to the second waist region.

In another aspect, the invention concerns a method of forming an absorbent article including the following steps: (1) providing a garment having a first waist region, a second waist region, and a crotch region positioned between and interconnecting the first and second waist regions; (2) bonding a first interlocking fastening component to the first waist region; (3) providing a second interlocking fastening component adapted for refastenable attachment to the first interlocking fastening component, the second interlocking fastening component comprising a backing structure formed of a resilient material and having a first major surface with a plurality of engaging elements projecting from the first major surface; (4) forming the first major surface with a concave configuration and a bending index of at least about 0.3 inch$^{-1}$; and (5) bonding the second interlocking fastening component to the second waist region.

Numerous features and advantages of the present invention will appear from the following description. In the description, reference is made to the accompanying drawings which illustrate preferred embodiments of the invention. Such embodiments do not represent the full scope of the invention. Reference should therefore be made to the claims herein for interpreting the full scope of the invention.

BRIEF DESCRIPTION OF THE DRAWINGS

FIG. 10 representatively shows a top view of an apparatus used to test components of disposable absorbent articles.

FIG. 11 representatively shows a side view of the apparatus shown in FIG. 10.

DETAILED DESCRIPTION OF THE PREFERRED EMBODIMENTS

Figure 1:
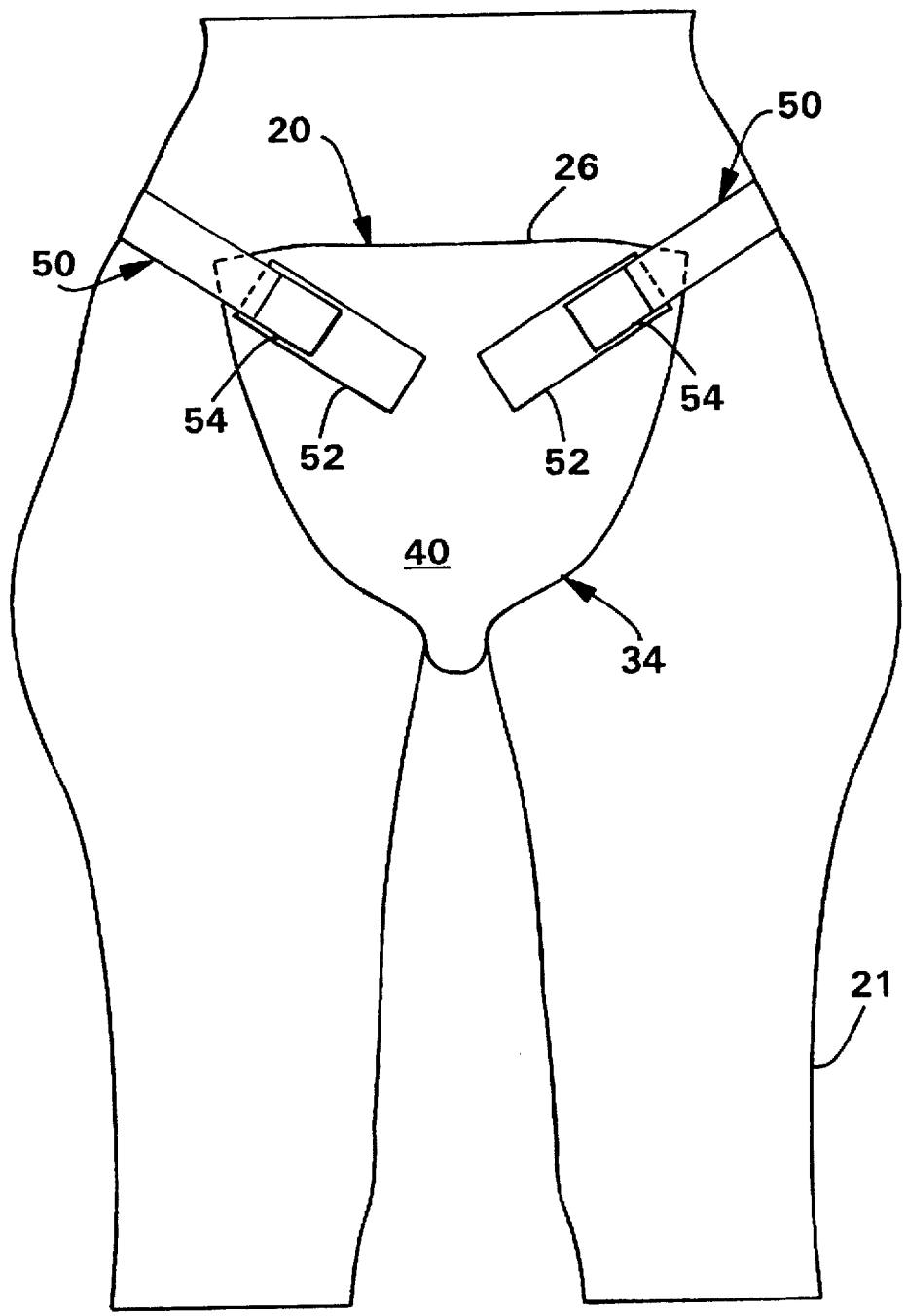
FIG. 1 representatively shows a front plan view of a disposable absorbent article according to the present invention positioned on an adult-sized mannequin.

With reference to FIGS. 1–5 and 7, an absorbent article formed according to the invention is shown for purposes of illustration as a disposable undergarment 20 for adult incontinence which is maintained in position about a wearer by an attachment system comprising a pair of strap members 50. As used herein, the term disposable includes being disposed of after use and not intended to be washed and reused. The undergarment 20 is shown in FIG. 1 positioned on a mannequin 21 to illustrate the position the undergarment assumes during use. The invention may also be embodied in other types of garments, such as other disposable absorbent articles, reusable absorbent articles, or the like.

Figure 3:
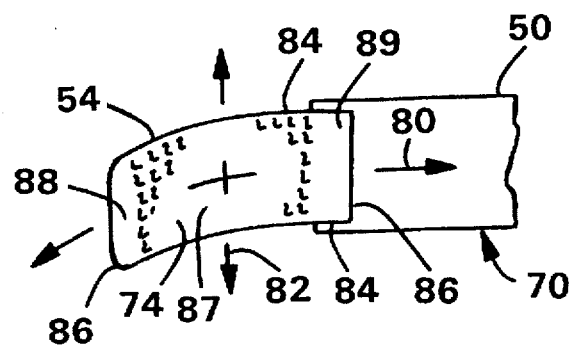
FIG. 3 representatively shows an enlarged perspective view of one end portion of the strap member shown in FIG. 2.
Figure 4:
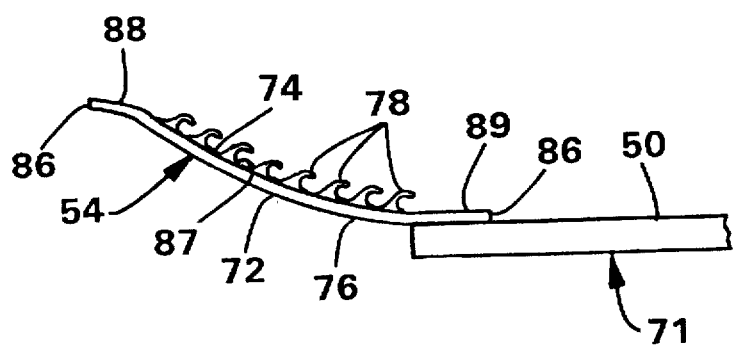
FIG. 4 representatively shows an enlarged section view taken generally from the plane of the line 4—4 in FIG. 2.
Figure 5:
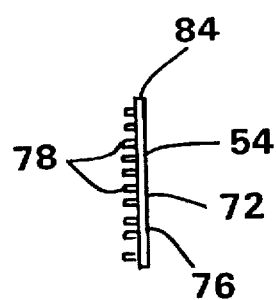
FIG. 5 representatively shows an enlarged section view taken generally from the plane of the line 5—5 in FIG. 2.

In general, the undergarment 20 includes first interlocking fastening components 52 disposed on the undergarment 20 and second interlocking fastening components 54 bonded to the strap members 50. The second interlocking fastening components 54 comprise a resilient backing structure 72 having a first major surface 74 including a plurality of engaging elements 78 (FIGS. 3–5). The first major surface 74 is adapted to have a concave shape in the direction of a primary meridian 80, in the direction of a secondary meridian 82, or in both directions. The concavity of the first major surface 74 is described in detail below and is characterized in terms of a bending index or an elevation of a central portion 87 of the surface 74.

Figure 7:
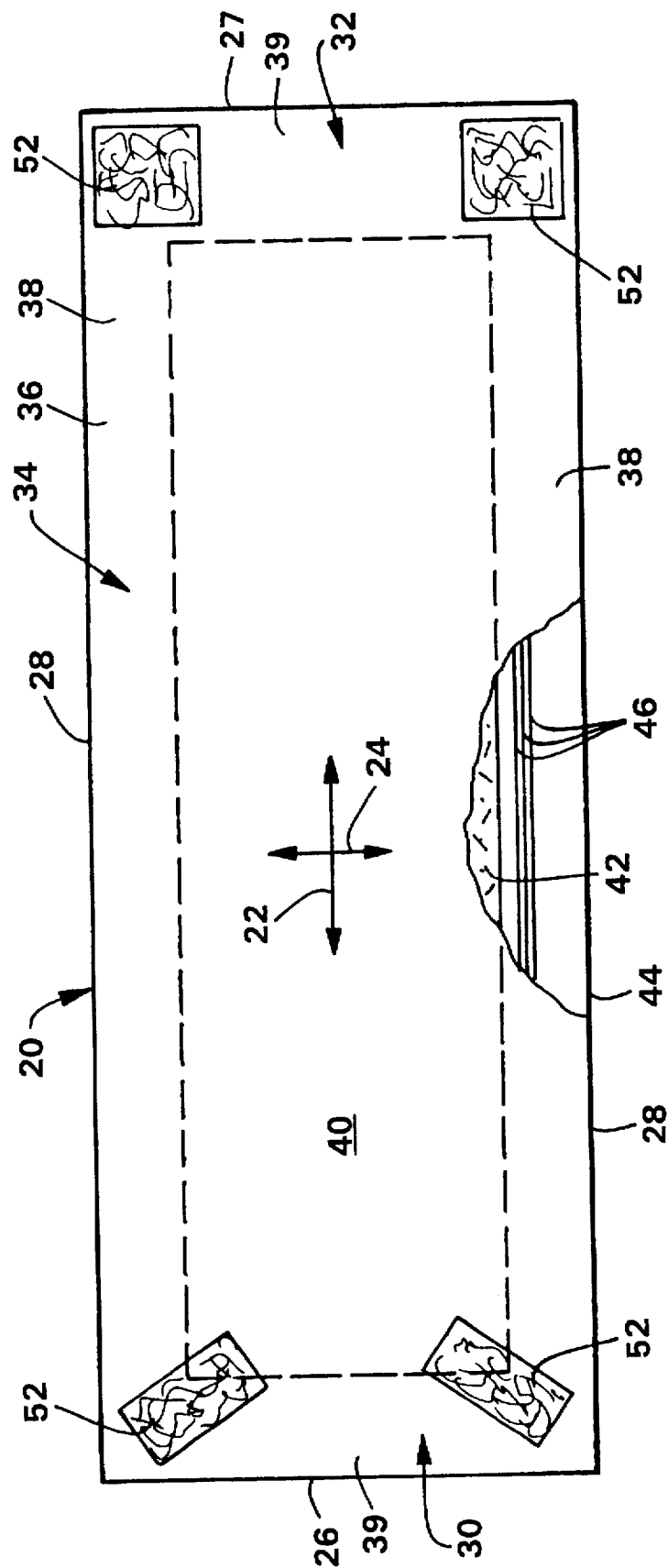
FIG. 7 representatively shows a plan view of a garment portion of the disposable absorbent article shown in FIG. 1, taken from the outer garment side of the absorbent article in a stretched and laid flat condition and with portions broken away for purposes of illustration.

With reference particularly to FIG. 7, the illustrated undergarment 20 defines a longitudinal axis or center line represented by arrow 22 and a transverse axis or center line represented by arrow 24. The longitudinal axis 22 generally corresponds to the machine direction of the garment during manufacture and the greatest planar dimension of the product. The undergarment 20 has opposite, front and back longitudinal end edges 26 and 27, and longitudinal side edges 28 that extend between the longitudinal end edges. The undergarment 20 includes a first or front waist region 30, a second or back waist region 32, and an intermediate, crotch region 34 positioned between and interconnecting the front and back waist regions.

The outer edges of the undergarment 20 define a periphery 36 in which the longitudinally extending side margins are designated 38 and the laterally extending end margins are designated 39. The end edges 26 and 27 and side edges 28 are shown as generally straight, but optionally, may be curvilinear and contoured.

The front waist region 30 is contiguous with the front end edge 26 and extends longitudinally inward therefrom toward the transverse center line 24 of the undergarment 20. The back waist region 32 is contiguous with the back end edge 27 and extends longitudinally inward therefrom toward the transverse center line 24. The waist regions 30 and 32 comprise those upper portions of undergarment 20 which, when worn, wholly or partially cover or encircle the waist or mid-lower torso of the wearer. The intermediate, crotch region 34 comprises that portion of undergarment 20 which, when worn, is positioned between the legs of the wearer and covers the lower torso of the wearer (FIG. 1). Thus, the crotch region 34 is the area where insults of urine typically occur in the undergarment or other disposable absorbent article.

The undergarment 20 includes a substantially liquid impermeable moisture barrier 40, an absorbent assembly 42 disposed on the moisture barrier, and a substantially liquid permeable bodyside liner 44 bonded to the moisture barrier to sandwich the absorbent assembly therebetween (FIG. 7). The moisture barrier 40 and bodyside liner 44 are desirably longer and wider than the absorbent assembly 42 so that the peripheries of the moisture barrier and bodyside liner may be bonded together using ultrasonic bonds, thermal bonds, adhesives, or other suitable means. The peripheries of the moisture barrier 40 and the bodyside liner 44 typically form the side and end margins 38 and 39 of the undergarment 20. The absorbent assembly 42 may be bonded directly to the moisture barrier 40 and/or the bodyside liner 44 using ultrasonic bonds, thermal bonds, adhesives, or other suitable means. As used herein, the term bonded refers to the joining, adhering, connecting, attaching, or the like, of two elements. Two elements will be considered to be bonded together when they are bonded directly to one another or indirectly to one another, such as when each is directly bonded to intermediate elements. The terms disposed, disposed on, disposed with, disposed at, disposed near and variations thereof are intended to mean that one element can be integral with another element, or that one element can be a separate structure bonded to or placed with or placed near another element.

The moisture barrier 40 desirably comprises a material that is formed or treated to be liquid impermeable. Alternatively, the moisture barrier 40 may comprise a liquid permeable material and other suitable means may be provided to impede liquid movement away from the absorbent assembly, such as a liquid impermeable layer (not shown) associated with the absorbent assembly 42. The moisture barrier 40 may also be gas permeable, such that gases encountered during use of the absorbent garment are able to pass through the material under ordinary use conditions, over either all or part of its surface area.

The moisture barrier 40 may comprise a single layer of material or a laminate of two or more separate layers of material. Suitable moisture barrier materials include films, wovens, nonwovens, laminates of films, wovens, and/or nonwovens, or the like. For example, the moisture barrier 40 may comprise a thin, substantially liquid impermeable web or sheet of plastic film such as polyethylene, polypropylene, polyvinyl chloride or similar material. The moisture barrier material may be transparent or opaque and have an embossed or matte surface. One particular material for the moisture barrier 40 is a polyethylene film that has a nominal thickness of about 0.025 millimeter and a systematic matte embossed pattern, and that has been corona treated on both sides. Another suitable moisture barrier material is an adhesive or thermal laminate comprising a cast or blown film formed of polypropylene, polyethylene or the like, and a spunbond web formed of polypropylene and polyethylene medium-crimped bicomponent fibers in a 50/50 side-by-side configuration.

The absorbent assembly 42 comprises materials adapted to absorb and retain liquid waste. The absorbent assembly 42 may comprise various absorbent materials, such as an airformed batt of cellulosic fibers (i.e., wood pulp fluff) or a coform material composed of a mixture of cellulosic fibers and synthetic polymer fibers. Polymer fibers may be incorporated, for example, in the manner described in U.S. Pat. No. 5,227,107 issued Jul. 13, 1993, to Dickenson et al. The absorbent assembly 42 may also include compounds to increase its absorbency, such as 0–95 weight percent of organic or inorganic high-absorbency materials, which are typically capable of absorbing at least about 15 and desirably more than 25 times their weight in water. Suitable high-absorbency materials are described in U.S. Pat. Nos. 4,699,823 issued Oct. 13, 1987, to Kellenberger et al. and 5,147,343 issued Sep. 15, 1992, to Kellenberger, which are incorporated herein by reference. High-absorbency materials are available from various commercial vendors, such as Dow Chemical Company, Hoechst Celanese Corporation, and Allied Colloids, Inc. The absorbent assembly 42 may also include tissue layers or acquisition or distribution layers to help maintain the integrity of fibrous absorbents or transport liquids (not shown).

The bodyside liner 44 is formed of a liquid permeable material so that liquid waste, and possibly semi-solid waste as well, can pass through the liner and be absorbed by the absorbent assembly 42. Suitable bodyside liners 44 may comprise a nonwoven web or sheet of wet strength tissue paper, a spunbonded, meltblown or bonded-carded web composed of synthetic polymer filaments or fibers, such as polypropylene, polyethylene, polyesters or the like, or a web of natural polymer filaments or fibers such as rayon or cotton. In addition, the bodyside liner 44 is desirably nonelastic and may be treated with a surfactant to aid in liquid transfer. In a particular embodiment of the invention, the liner 44 comprises a nonwoven, spunbond polypropylene fabric composed of about 2.8–3.2 denier fibers formed into a web having a basis weight of about 22 gsm and density of about 0.06 gm/cc. The fabric is surface treated with about 0.28 weight percent of a surfactant commercially available from Rohm and Haas Co. under the trade designation Triton X-102. As used herein, the term fabric is used to refer to all of the woven, knitted and nonwoven fibrous webs. The term nonwoven web means a web of material which is formed without the aid of a textile weaving or knitting process.

The undergarment 20, which is in a stretched and laid flat condition in FIG. 7, is illustrated as having a rectangular periphery 36. Of course, the undergarment 20 may optionally be hourglass-shaped, I-shaped, T-shaped, or irregularly-shaped. The general shape of the absorbent assembly 42 may correspond to the shape of the undergarment 20 or assume a different shape. For example, the undergarment 20 may include a relatively short absorbent assembly and separate liquid handling layers in the waist regions (not shown) as disclosed in U.S. patent application Ser. No. 08/515,505 titled "Absorbent Article Having Improved Waist Region Dryness And Method Of Manufacture" and filed Aug. 15, 1995 by L. LeMahieu et al. and assigned to the assignee of the present application.

Desirably although not necessarily, the undergarment 20 also includes leg elastic members 46 (FIG. 7) to draw and hold the side margins 38 of the undergarment 20 against the legs of the wearer and form a seal therewith. As used herein, the terms elastic, elasticized and elasticity mean that property of a material by virtue of which it tends to recover its original size and shape after removal of a force causing a deformation. The elongated leg elastic members 46 are longitudinally orientated in each 0 side margin 38, extending toward the front and back end edges 26 and 27. The leg elastic members 46 are positioned in the illustrated embodiment between the moisture barrier 40 and the bodyside liner 44. Using ultrasonic bonds, adhesives, thermal bonds, or other suitable means, the leg elastic members 46 are attached in a stretched condition to the moisture barrier 40, the bodyside liner 44, or both, in either a straight or a curved shape. Alternatively, the leg elastic members 46 may be attached in a relaxed state to a gathered portion of the moisture barrier 40, the bodyside liner 44, or both.

The leg elastic members 46 may be formed of a dry-spun coalesced multifilament elastomeric thread sold under the tradename LYCRA and available from E.I. Du Pont de Nemours and Company. Alternately, the elastic members may be formed of other typical elastics utilized in the undergarment-making art, such as a thin ribbon of natural rubber, a stretch bonded laminate material comprising a prestretched elastic meltblown inner layer sandwiched between and bonded to a pair of spunbond polypropylene nonwoven webs, or the like. Elasticity could also be imparted to the absorbent article by extruding a hot melt elastomeric adhesive between the moisture barrier 40 and the liner 44. Other suitable elastic gathering means are disclosed in U.S. Pat. Nos. 4,938,754 to Mesek and 4,388,075 to Mesek et al.

The attachment system in the illustrated embodiment includes a pair of strap members 50 that are releasably attached to the front and back waist regions 30 and 32 to support the undergarment 20 about the body of the wearer. Attachment systems of this general type are disclosed in U.S. Pat. No. B1 4,315,508 to Bolick, which is incorporated herein by reference. The present fastening system, which is designed to releasably attach the strap members 50 to the undergarment 20 with a minimum number of pop-offs during use, will now be described in greater detail.

The illustrated fastening system includes a plurality of first and second interlocking fastening components 52 and 54 that are adapted to refastenably connect to one another. The first interlocking fastening components 52 consist of four separate elements bonded to the moisture barrier 40, and the second interlocking fastening components 54 consist of four separate elements bonded to the two strap members 50.

The interlocking fastening components 52 and 54 have surfaces that are refastenably connectable. The term refastenably connectable and variations thereof are used herein to mean that the surfaces are adapted to repeatedly, releasably engage one another. Specifically, one surface of each of the interlocking fastening components 52 and 54 comprises a plurality of engaging elements that project from that surface. The engaging elements of one interlocking fastening component 52 or 54 are adapted to repeatedly engage and disengage the engaging elements of the other interlocking fastening component. Suitable engaging elements for such interlocking materials include self-engaging geometric shaped materials, such as hooks, loops, bulbs, mushrooms, arrowheads, balls on stems, male and female mating components, or the like. As used herein, the term releasably engaged and variations thereof refer to two elements being connected or connectable such that the elements tend to remain connected absent a separation force applied to one or both of the elements, and the elements being capable of separation without substantial permanent deformation or rupture.

The engagement of the components 52 and 54 is accomplished mechanically rather than adhesively, and the components are adapted to resist disengagement in a shear mode yet release relatively easy from one another in a peel mode. The shear mode of a fastener release refers to forces tending to separate the mechanical interlocking fastening components (such as a hook-and-loop material) when the components are subjected to opposing forces in the plane of attachment of the components, and the peel mode of a fastener release refers to forces tending to separate the mechanical interlocking fastening components when one component is subjected to a force perpendicular to the plane of attachment of the components. As used herein, the term force includes a physical influence exerted by one body on another which produces acceleration of bodies that are free to move and deformation of bodies that are not free to move.

In the illustrated embodiment, the first interlocking fastening components 52 are formed of a loop material and will also be referred to as loop fasteners 52, and the second interlocking fastening component 54 are formed of a hook material and will also be referred to as hook fasteners 54. These fasteners 52 and 54 comprise the complementary, mating components of a hook-and-loop fastening system.

Figure 8:
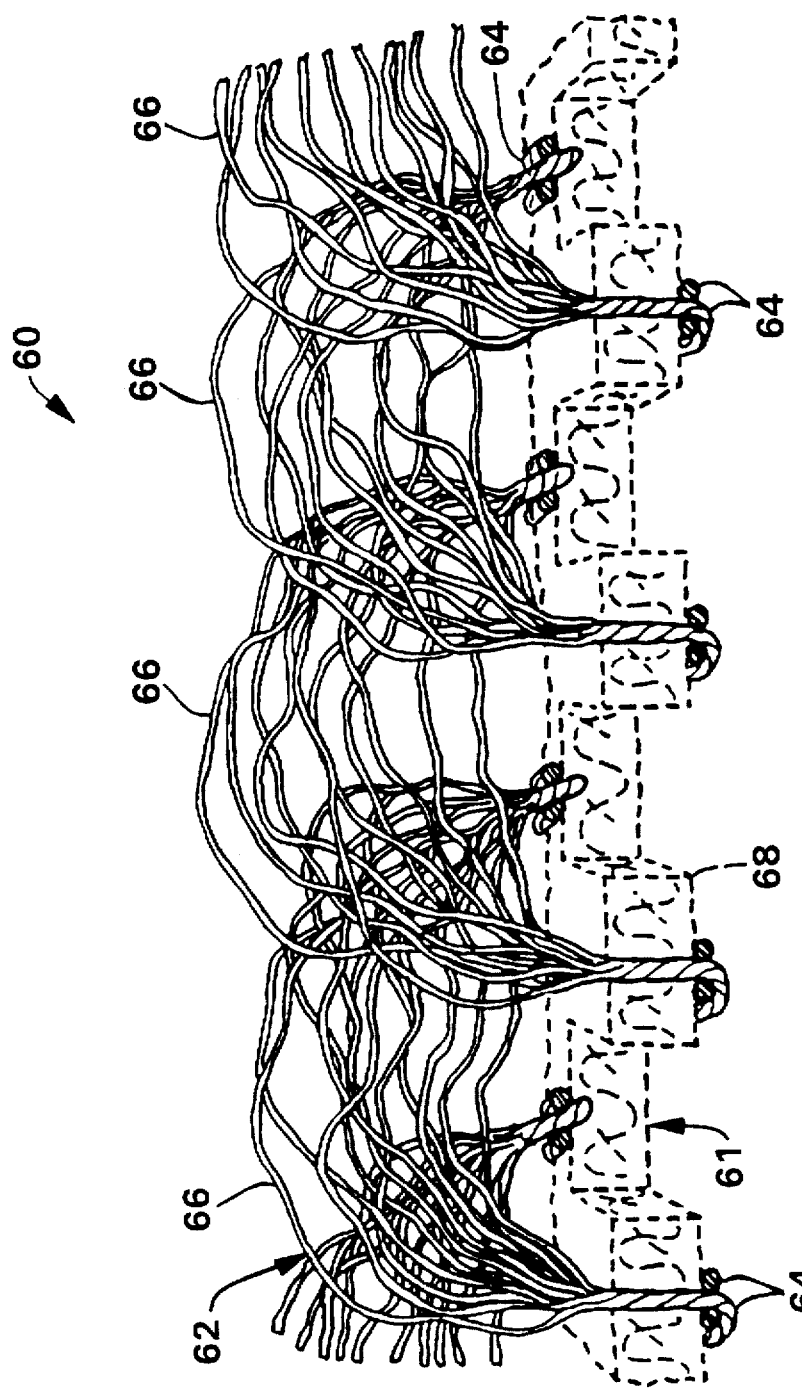
FIG. 8 representatively shows an enlarged section view of an exemplary loop material.

The term loop material is intended to mean any fabric having a base or backing structure and a plurality of loop members extending upwardly from at least one surface of the backing structure. An illustrative loop material 60 is representatively shown in FIG. 8. The loop material 60 is a flexible fabric material having opposite major surfaces designated first major surface 61 and second major surface 62. The loop material 60 comprises yarns 64 that are arranged to provide a raised loop construction in which the fabric is stabilized so that engaging elements, that is loops 66, are erect from the fabric backing 68. As used herein, the term flexible refers to materials which are compliant and which will readily conform to the general shape and contours of the wearers body.

The loop material 60 may be formed of any suitable material, such as acrylic, nylon or polyester, and may be formed by methods such as warp knitting, stitch bonding or needle punching. The loop material 60 can be stabilized through napping, thermosetting or the like so that the individual loops 66 are erect from the fabric base 68. The loop fasteners 52 can also be any suitable material having non-woven loops thereon. The loop material 60 may optionally include a sizing (not shown), such as a vinyl acetate copolymer sizing available from National Starch and Chemical Corp. under the trade designation RESYN 5904, applied by mist deposition or other suitable means to the backing 68 to a final concentration of less than about 4 weight percent.

In a preferred embodiment, the first interlocking fastening components 52 are formed of a loop material 60 having a two bar warp knit construction, with from 21 to 41 courses per inch (8–16 per cm.) and from 26 to 46 wales per inch (10–18 per cm.), of polyester yarn. In particular, about 15–35 percent of the yarns may be composed of yarn having about 1–30 individual filaments therein and having a yarn denier within the range of about 15–30 d (denier). In addition, about 65–85 percent of the yarns may be composed of yarn having about 1–30 individual filaments therein and having a yarn denier within the range of about 20–55 d. Also, the loops may particularly be formed with a loop height from about 2 to about 2.5 millimeters. The loop caliper may be from about 0.010 to about 0.040 inch (0.25–1 mm.) and the basis weight may be from about 1.0 to about 3.0 ounces per square yard (34–102 grams per square meter). One particular loop material 60 which has been found suitable for the loop fasteners 52 is identified as No. 19902 and is available from Guilford Mills of Greensboro, N.C.

As shown in FIGS. 1 and 7, the first interlocking fastening components or loop fasteners 52 are bonded to the surface of the moisture barrier 40 that is remote from the bodyside liner 44. Each of the loop fasteners 52 is rectangular, although the loop fasteners may alternatively be square, round, oval, curved or otherwise nonrectangularly shaped. The loop fasteners 52 in each waist region 30 and 32 are desirably separated from one another and positioned adjacent the opposite sides edges 28. Desirably although not necessarily, the loop fasteners 52 are also spaced from the front and back end edges 26 and 27 and the side edges 28 by at least about 0.25 inch (6.5 min.). Alternatively, there may be a greater number or a lesser number of loop fasteners 52 bonded to the moisture barrier 40 (not shown). Still alternatively, the moisture barrier itself may be constructed of a interlocking material so that the strap members 50 may be attached directly to the moisture barrier (not shown).

The loop fasteners 52 in the front and back waist regions 30 and 32 may be the same size and be symmetrically positioned. More desirably, however, it has been determined that the particular loop fasteners 52 disclosed herein provide adjustability for the attachment system and at the same time promote the proper orientation of the undergarment 20 on the wearer. In particular, the loop fasteners 52 are desirably attached at specified angles in relation to the longitudinal and transverse axes 22 and 24 of the undergarment 20 in order to promote a proper orientation of the garment on the wearer.

The loop fasteners 52 in the front waist region 30 are desirably rectangular in shape measuring approximately 1.25 inches by 3.38 inches (3 by 9 cm.). Each loop fastener 52 in the front waist region 30 is bonded to the moisture barrier 40 such that the longitudinal axis of the fastener is directed generally toward the nearest corner of the undergarment 20 and forms an angle in the range of from about 25 to about 45 degrees with the transverse axis 24. The term longitudinal axis in reference to the fastener 52 is used to mean the axis parallel to the longer dimension of the fastener.

Each loop fastener 52 in the back waist region 32 is desirably at least 1 inch by 1 inch (25 by 25 mm.), providing a surface area of at least about 1 in$^2$ (6.25 cm$^2$). For example, the loop fasteners 52 in the back waist region 32 may be rectangular and measure 1.5 inch by 2.0 inch (38 by 51 mm.), with the longer dimension of the fastener aligned with the transverse axis 24 of the undergarment 20. Alternately, the loop fasteners 52 in the back waist region 32 could be formed as a single pad of loop material attached across the back waist region 32 (not shown).

The loop tip orientation of the loop fasteners 52 has been found to affect performance of the attachment system. The preferred loop material 60 will have a loop tip orientation (not shown) in a single direction. As used herein, loop tip orientation refers to the general direction in which the tips of the loop members 66 are bent. This direction, which will be in the plane of the loop material, is caused by the napping process used to make the loop material. However, the loop tip orientation may be generated by other processes as well, such as brushing, scraping, nipping, rolling, pressing, differential creeping, combing and so forth. The loop tip orientation of a loop material can be established by selecting appropriate manufacturing processes and equipment as known in the art.

Desirably, the loop tip orientation of either loop fastener 52 in the front waist region 30 is generally perpendicular to the longitudinal axis of the fastener and directed toward the front end edge 26 of the undergarment 20. Furthermore, the loop tip orientation of either loop fastener 52 in the back waist region 32 is desirably generally parallel to the longitudinal axis 22 of the undergarment 20 and directed toward the opposite or front end edge 26 of the undergarment. Alternately, however, the loop tip orientation of either loop fastener 52 in the back waist region 32 could be generally parallel to the transverse axis 24 of the undergarment 20 and directed toward the other loop fastener 52 in the back waist region. Further arrangements of the loop fasteners are disclosed in U.S. Pat. No. 5,386,595 to Kuen et al., which is incorporated herein by reference.

Desirably although not necessarily, the loop fasteners 52 are bonded to the moisture barrier 40 with an adhesive substance. The adhesive substance may comprise any suitable adhesive such as a hot melt, or the like. By way of illustration, the adhesive substance may comprise a styrene-isoprene-styrene rubber block copolymer based adhesive containing a rosin ester tackifying resin. One suitable adhesive is available from Findley Adhesives, Inc. of Wauwatosa, Wis., USA, under the trade designation H2122. The adhesive substance may include zones having different basis weights of adhesive or other beneficial arrangements as disclosed in U.S. Pat. No. 5,476,702 to P. Datta et al., which is incorporated herein by reference.

Figure 2:
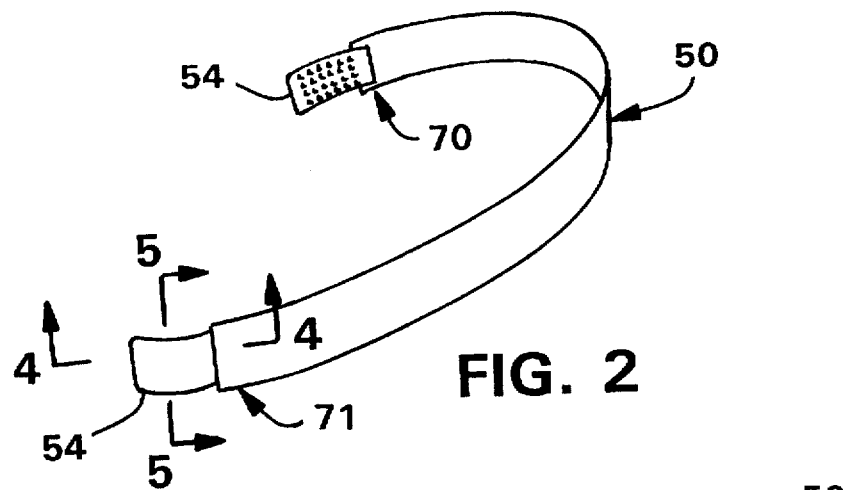
FIG. 2 representatively shows a perspective view of one of the strap members of the disposable absorbent article of FIG. 1.

With particular reference to FIGS. 1–3, the strap members 50 are each generally rectangular strips of material having opposite forward and rearward end portions 70 and 71. The strap members 50 are preferably formed of an elastic material, which is capable of stretching to approximately 2.8 to 3 times its relaxed length. The strap members 50 preferably have a longer length dimension of from about 6 inches to about 16 inches (15–41 cm.), and a smaller width dimension of from about 0.5 inch to about 2 inches (1–5 cm.). For example, each strap member 50 may be 11 inches (28 cm.) long and 1 inch (2.5 cm.) wide. The cut ends of the strap members 50 may be bonded by ultrasonic bonds, adhesives or other suitable means to prevent raveling.

The second interlocking fastening components or hook fasteners 54 are attached at each end portion 70 and 71 of each strap member 50, on the same side of the strap member. The hook fasteners 54 desirably comprise a single-sided hook material and form the hook component of the hook-and-loop attachment system. The term hook material is intended to mean any fabric or material having a base or backing structure and a plurality of hook members extending upwardly from at least one surface of the backing structure.

In contrast to the first interlocking fasteners 52 which desirably comprise a flexible fabric, the second interlocking fasteners 54 advantageously comprise a resilient material to minimize unintentional disengagement of the fastener components as a result of the second interlocking fastening component becoming deformed and catching on clothing or other items. The term resilient as used herein refers to an interlocking material having a predetermined shape and the property of the interlocking material to resume the predetermined shape after being engaged and disengaged from a mating, complementary interlocking material. A test to characterize the resiliency of an interlocking material is presented hereinafter.

With particular reference to FIGS. 3–5, each hook fastener 54 comprises a backing structure 72 having a first major surface 74 and an opposite second major surface 76. A plurality of engaging elements in the form of hooks 78 project upwardly from the first major surface 74. Each hook fastener 54 has a primary meridian 80 parallel to the length dimension of the strap member 50 when laid flat and a secondary meridian 82 which intersects the primary meridian at a 90 degree angle (FIG. 3). The terms primary meridian and secondary meridian are used herein to refer to the curves defined by the intersection of the backing structure 72 and perpendicular planes containing the longitudinal and transverse axis of the hook fastener 54. The primary and secondary meridians 80 and 82 are desirably nonlinear, but in particular embodiments one or the other may be linear. Opposite side edges 84 of the backing structure 72 extend generally parallel to the primary meridian 80 and opposite end edges 86 extend between the side edges. A central portion 87 of the backing structure 72 is disposed between the opposite side edges 84 and between the opposite end edges 86.

The hook fasteners 54 may be of a variety of shapes, such as rectangular and measuring about 0.875 inch by about 1.125 inches (2.2 by 2.9 cm.). As best illustrated in FIGS. 3 and 4, each hook fastener 54 may include a grasping region 88 that is somewhat rounded and void of hooks. The grasping region 88 provides a convenient surface for grasping the hook fastener 54 to remove it from engagement with the loop fastener 52. The hook fasteners 54 may be positioned in full face-to-face contact with the strap members 50 (not shown), or positioned such that hook fasteners extend past the ends of the strap members (FIGS. 1–4). The hook fasteners 54 may be attached to the strap members 50 by ultrasonic bonds, adhesives, stitches or other suitable means, and may include an attachment region 89 that is void of hooks. For example, the hook fasteners 54 may be ultrasonically bonded to the strap members 50 during which process hooks present adjacent one end edge 86 are melted into the backing structure 72 to form the attachment region 89.

Suitable hook material may be molded or extruded of nylon, polypropylene or another suitable material. Desirable stiffness levels of the hook material may be obtained from polymeric materials having a flexural modulus of about 70,000–120,000 pounds per square inch ($4.83 \times 10^8$–$8.27 \times 10^8$ nt/m$^2$) and a Shore hardness value within the range of about D-40 to D-80, such as D-61. The hook fasteners 54 desirably contain uni-directional hooks, with the machine direction of the hooks aligned with the primary meridian 80, and the hooks directed toward the opposite end portion 70 or 72 of the strap member 50. One suitable single-sided hook material for the hook fasteners 54 is available from Velcro Industries B.V., Amsterdam, Netherlands or affiliates thereof, and is identified as HTH-840 with 22 Series hooks in a uni-directional hook pattern.

The shape, density and polymer composition of the hooks may be selected to obtain the desired peel and shear force resistance values between the hook fasteners 54 and the loop fasteners 52. One skilled in the art would recognize, for instance, that a more aggressive hook material may comprise a material with a greater average hook height, a greater percentage of directionally-aligned hooks, or a more aggressive hook shape. As one example, the density of the hook members may be more than 50 hooks per square inch (8 per square cm.), and more particularly within the range of about 440 to about 1040 hooks per square inch (68–161 per square cm.), such as about 740 hooks per square inch (115 per square cm.). The row density may be within the range of about 20 to about 60 rows per linear inch of width (8–24 per linear cm.), such as about 40 rows per linear inch of width (16 per linear cm.). The hook members may be hook-shaped, mushroom-shaped, arrow-shaped or any other desired shape.

Applicants have discovered that providing the resilient second interlocking fastening components 54 with a concave configuration increases the resistance of the fastening system to pop-offs. In particular, the backing structures 72 are desirably formed or treated so that the second interlocking fastening components 54 have a concave shape, viewed with respect to the major surface 74 that includes the engaging elements 78. The term concave is used herein to mean curved like the inner surface of a sphere, and is used to relate to either a line or surface. Thus, a backing structure 72 may be concave in the direction of only one of the primary or secondary meridians 80 or 82 or concave in the direction of both the primary and secondary meridians.

The degree of curvature or concavity of the second interlocking fastening components 54 may be characterized in terms of a bending index. As used herein, the term bending index refers to a measurement of the curvature of the first major surface 74 of the backing structure 72. The bending index is the inverse of the radius of curvature of the first major surface 74. One suitable method for measuring the radius of curvature of the first major surface 74 is set forth in greater detail below in connection with the examples. The formula for the bending index is as shown below:

Bending index (inch$^{-1}$)=1÷Radius of curvature (inch).

Figure 6:
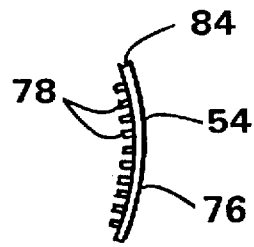
FIG. 6 representatively shows an enlarged section view similar to FIG. 5 but illustrating an alternative embodiment of the invention.

In one aspect of the invention, the first major surface 74 of the backing structure 72 is concave with a bending index of at least 0.3 inch$^{-1}$ (0.12 cm$^{-1}$) The concavity may be in the direction of the primary meridian 80 as illustrated in FIGS. 3 and 4. The backing structure 72 is said to be concave in the direction of the primary meridian 80 when the backing structure is curved about an axis that is generally parallel to the secondary reeddian 82. Alternatively, the backing structure 72 may be concave in the direction of the secondary reeddian 82 as illustrated in FIG. 6, whereby the backing structure is curved about an axis that is generally parallel to the primary meridian 80. Still alternatively, the backing structure 72 may be concave in the direction of both the primary meridian 80 and the secondary meridian 82, in which case the first major surface 74 is three-dimensionally concave. One advantage of forming the backing structure 72 so that it is concave in the direction of the secondary meridian 82 is that the user can more easily get a finger or fingernail under the fastening component to disengage the fastener.

By way of illustration, the bending index of the first major surface 74 may be from 0.3 to about 1.1 inch$^{-1}$(0.12–0.43 cm$^{-1}$). More particularly, the bending index of the first major surface 74 is desirably at least about 0.5 inch$^{-1}$ (0.2 cm$^{-1}$), such as about 0.5 to about 1.1 inch$^{-1}$ (0.2–0.43 cm$^{-1}$). In one desirable embodiment of the invention, the first major surface 74 is concave with a bending index in the direction of the primary meridian 80 of at least about 0.5 inch$^{-1}$ (0.2 cm$^{-1}$) and a bending index in the direction of the secondary meridian 82 of at least about 0.5 inch$^{-1}$ (0.2 cm$^{-1}$). For example, in one particularly desirable embodiment, the first major surface 74 is concave with a bending index in the direction of the primary meridian 80 of at least about 0.6 inch$^{-1}$ (0.24 cm$^{-1}$) and a bending index in the direction of the secondary meridian 82 of at least about 1 inch$^{-1}$ (0.4 cm$^{-1}$).

The degree of curvature or concavity of the second interlocking fastening components 54 may alternatively be characterized in terms of the elevation of the central portion 87 of the backing structure 72. The elevation may be determined by selecting three points that lie in a reference meridian of the backing structure 72, which reference meridian is parallel to either the primary meridian 80 or the secondary meridian 82. The three points that are selected from the reference meridian are (1) a first endpoint, (2) an intermediate point, and (3) a second endpoint, with the intermediate point located between the endpoints. The elevation of the central portion 87 of the backing structure 72 is the length of a perpendicular line segment extending from the intermediate point to a reference plane containing the first and second endpoints.

To characterize the curvature or concavity in the direction of the primary meridian 80 in terms of the elevation of the central portion 87, the reference meridian selected is generally parallel to the primary meridian. The first and second endpoints may correspond to the opposite end edges 86 of the backing structure 72 or peripheral points inward thereof. Conversely, to characterize the curvature in the direction of the secondary meridian 82, the reference meridian selected is generally parallel to the secondary meridian. Here, the first and second endpoints may correspond to the opposite side edges 84 of the backing structure 72 or peripheral points inward thereof.

The elevation of the central portion 87 of the backing structure 72 can also be related to the radius of curvature by the following formula:

$$R=(c^2+4h^2)/8h;$$

where

R=the radius of curvature;

c=the linear distance between the first and second endpoints; and h=the length of a perpendicular line segment extending from the center point to the reference plane containing the first and second endpoints.

In one aspect of the invention, the concave first major surface 74 of the backing structure 72 is shaped such that the central portion 87 is elevated by at least about 1.0 millimeter from a plane containing opposite, outwardly positioned peripheral points. In particular embodiments, the central portion 87 is elevated by at least about 1.0 millimeter from the opposite side edges 84, or from the opposite end edges 86, or from both the side and the end edges. For example, the central portion 87 may be elevated by about 1.0 to about 2.0 millimeters from a plane containing the opposite edges 84 or 86. More particularly, the central portion 87 is elevated by at least about 1.5 millimeters, such as about 1.5 to about 2.0 millimeters, from the opposite side edges 84, or from the opposite end edges 86, or from both the side and the end edges. As used herein, the terms inward and outward refer to positions relative to the center of the backing structure 72, and particularly transversely and/or longitudinally closer to or away from the longitudinal and transverse center of the backing structure.

The elevation of the central portion 87 of the backing structure 72 in relation to the direction of either the primary meridian 80 or the secondary meridian 82 will vary depending on the reference locations selected. In particular embodiments, the side and end edges 84 and 86 may be used as the reference locations. For purposes of the present invention, the elevation of the central portion 87 of an individual fastening component 54 is determined by selecting the reference locations that provide the greatest elevation value. Further, the elevation value of a fastening component 54 as employed for purposes of the present invention should be based on the average value obtained from 10 randomly-selected fastening components of the same type. Of course, the curvature of the second interlocking fastening component 54 is measured when the fastener is not attached to another interlocking material.

The backing structure 72 is desirably constructed to enhance the ability of the second interlocking fastening component 54 to retain a concave configuration after repeated uses. Specifically, the backing structure 72 is desirably constructed so as to retain a bending index of at least about 0.3 inch$^{-1}$, or a central elevation of at least about 1.0 millimeter, after 15 attachment and detachment cycles of the fastening components 52 and 54. Suitable fastening components 54 that have retained this degree of curvature have been constructed of polypropylene or nylon. Further, the composition of the backing structure 72 could be modified by imparting sterically hindered functional groups such as phthalic acid or the like, thereby forming polyesters or the like, for example polymers identified by the tradenames MYLAR and KEVLAR available from E.I. Du Pont de Nemours and Company, of Wilmington, Del., and NOMEX available from A. Meyers & Sons Corp., of New York, N.Y. Desirably, the backing structure 72 comprises a molded material, for example one that is cast from softened polymeric resins. Further, the backing structure 72 also suitably possesses an average Gurley stiffness of at least about 250 milligrams and less than about 3000 milligrams. Additionally, while the thickness of the backing structure 72 may vary considerably, it is generally desirable for the backing structure to have a thickness of from about 0.1 to about 0.5 millimeters. A shape retention test for determining the ability of a backing structure 72 to retain its shape is described below in relation to specific examples.

In use, the undergarment 20 is positioned on the body of the wearer and secured in position using the attachment system. The wearer can engage one hook fastener 54 of each strap member 50 with one of the loop fasteners 52 in the back waist region 32. After stretching or relaxing the strap members 50 to obtain the desired tension therein, the wearer can then engage the opposite hook fasteners 54 of each strap member 50 with one of the corresponding loop fasteners 52 in the front waist region 30. The angled orientation of the loop fasteners 52 prompts the wearer to secure the hook fasteners 54 so that the strap members 50 are aligned with the longitudinal axis of the front loop fasteners 52, beneficially causing the strap members to be positioned toward the hips of the wearer.

The concavity of the resilient hook fastening components 54 minimizes the likelihood that those components will pop-off when clothing is put on or removed. Instead of projecting away from the body of the wearer, the edges and corners of the resilient, contoured hook fasteners 54 penetrate deeply into the mating interlocking materials. This ensures that clothing or other materials passing over the hook fasteners 54 are less likely to snag on protruding edges and corners. This feature of the present invention is particularly significant because underpants or other clothing may be pulled on or taken off numerous times while the undergarment 20 is being worn. Desirably, the resilient backing structure 72 is adapted to retain its concave shape for at least 15 attachment and detachment cycles of the interlocking fastening components, so that the improved resistance to pop-offs is sustained during multiple uses.

Figure 9:
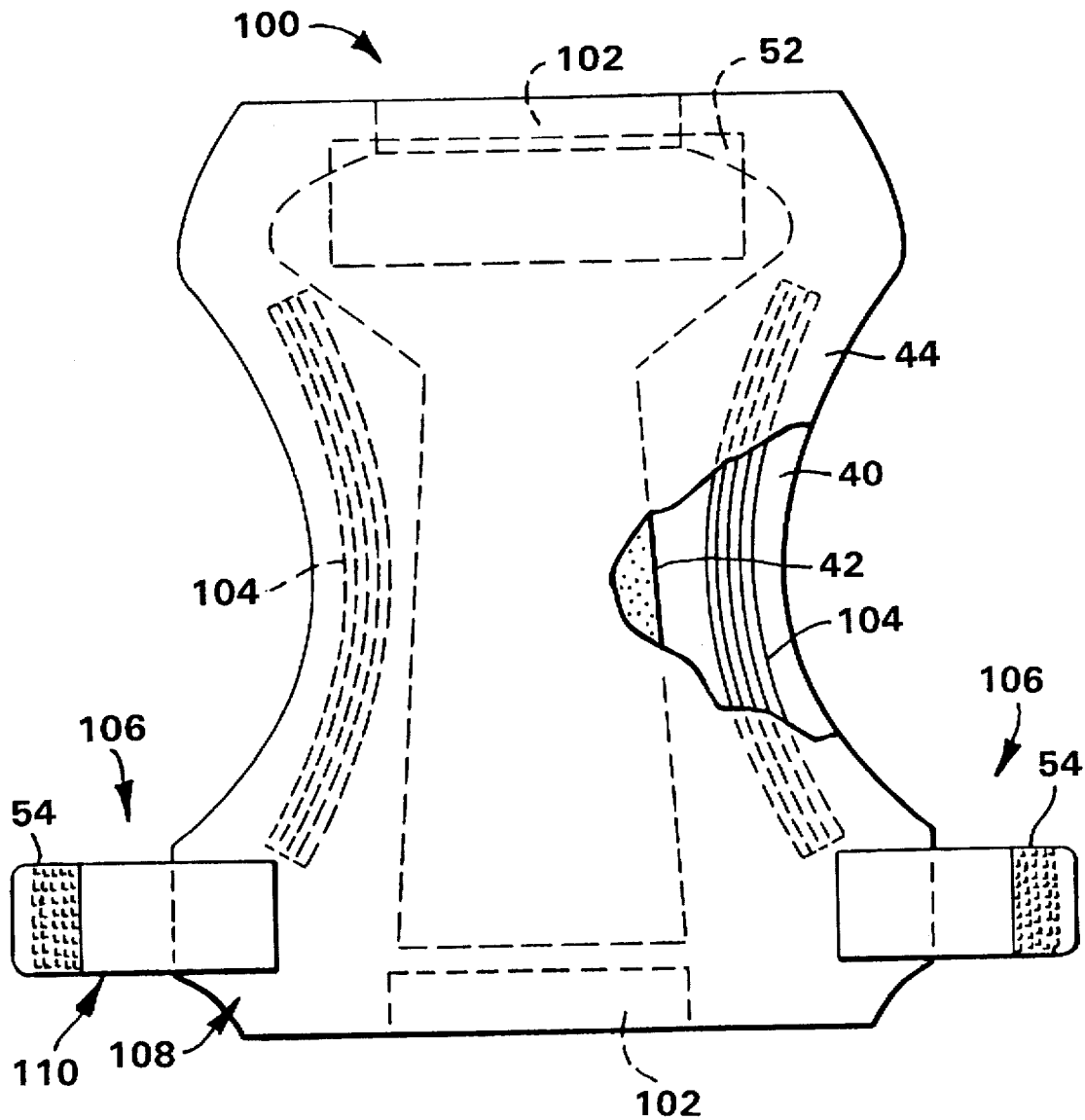
FIG. 9 representatively shows a plan view of an alternative disposable absorbent article according to the present invention, taken from the inner bodyside of the absorbent article in a stretched and laid flat condition and with portions broken away for purposes of illustration.

An alternative absorbent article according to the present invention is illustrated by a diaper 100 in FIG. 9, where components similar to those previously described have the same reference numeral. The diaper 100 includes a moisture barrier 40, a bodyside liner 44, and an absorbent assembly 42 disposed between the moisture barrier and bodyside liner. The diaper 100 may optionally contain waist elastics 102 and leg elastics 104. The diaper 100 also comprises fastening tabs 106 having a manufacturers bond end 108 bonded to the diaper and a users end 110 adapted to secure the diaper about the waist of the wearer. A first interlocking fastening component such as loop fastener 52 is bonded to the moisture barrier 40 in the waist region opposite the fastening tabs 106.

The user's end 110 refers to the portion of the fastening tab 106 that is used by the consumer to fasten the diaper about the waist of the wearer. The user's end 110 comprises an interlocking fastening component such as the hook fastener 54 illustrated in FIG. 9 that is adapted to refastenably attach to the loop fastener 52. The hook fastener 54 is desirably formed with a concave curvature in the direction of its primary meridian, in the direction of its secondary meridian, or both, as described above in relation to FIGS. 1–6.

In general, concave interlocking fastening components 54 having the above-described properties may be used with a variety of disposable absorbent products. Examples of diaper configurations, for instance, are disclosed in U.S. patent application Ser. No. 08/168,615 by T. Roessler et al., filed Dec. 16, 1993, and titled "Dynamic Fitting Diaper"; and U.S. patent application Ser. No. 08/288,167 by E. D. Johnson et al., filed Aug. 12, 1994, and titled "Diaper With Improved Lateral Elongation Characteristics". The concave interlocking fastening components 54 may also be employed on absorbent articles that use a belt or single strap system (not shown). Examples of fitted brief configurations are disclosed in U.S. Pat. No. 4,500,316 to Damico.

Each of the foregoing or similar embodiments of the invention may be constructed by providing each of the individual components and bonding them together in the manner set forth above. The concave second interlocking fastening components 54 may be formed originally in a concave configuration or formed originally in a generally flat shape and later formed in a concave configuration.

One aspect of the present invention relates to the method of forming the first major surface 74 of the backing structure 72 of the second interlocking fastening component 54 into a concave configuration. In one particular embodiment, the method of forming the first major surface 74 with a concave configuration employs an aluminum block with a depression formed in one surface. The depression may be created with a grinder that is rotated to provide a three-dimensional depression having a diameter of about 4.5 inches (11.4 cm). The aluminum block is heated to approximately the softening point of the thermoplastic backing structure 72. As used herein, the term thermoplastic describes a material that softens when exposed to heat and which substantially returns to a nonsoftened condition when cooled to room temperature. The backing structure is placed against the heated aluminum block with the engaging elements 78 disposed away from the block. The backing structure is maintained against the block for a dwell time that enables the particular backing structure 72 to assume the shape of the depression. The backing structure 72 is then slowly lifted from the heated block and allowed to cool slowly. In one particular embodiment, the backing structure 72 comprises a polypropylene structure, the block is heated to approximately 308 degrees Fahrenheit (153° C.), and the dwell time is about 4 to 5 seconds.

Numerous variations of the foregoing method are possible. For example, heated structures other than the aluminum block referenced above may be used to mold the backing structure 72. Also, the shape of the depression may be adjusted to control the concavity of the resulting backing structure 72, as would now be apparent based on the present disclosure. Further, the backing structure 72 may comprise a molded material that is formed initially in a concave configuration or processed immediately after formation into a concave configuration.

Having thus described the present invention and the process for making it, a series of examples were prepared to give a more detailed understanding of the invention. These examples and the test procedures for measuring them are set forth below. The particular amounts, proportions, compositions and parameters are meant to be exemplary, and are not intended to specifically limit the scope of the invention.

EXAMPLES

A simulation test was conducted to compare under simulated use conditions the operation of strap members with concave hook fasteners to strap members with generally flat hook fasteners. The strap members were tested in a laboratory with identical undergarments 20 having the general configuration as shown in FIG. 7. The strap members 50 with concave hook fasteners 54 are referred to as Example A Straps, and the strap members with generally flat hook fasteners are designated Control A Straps.

The undergarments 20 used in this test included a moisture barrier 40 which comprised an adhesive laminate of a polyethylene film inner layer and a spunbond nonwoven outer layer. An absorbent assembly 42 was disposed on the moisture barrier 40 and a spunbond polypropylene bodyside liner 44 was disposed on the absorbent assembly. The bodyside liner 44, absorbent assembly 42 and moisture barrier 40 were bonded together using a construction adhesive. The undergarments also included leg elastic members 46 secured along the two side margins 38 of the garment.

The fastening system for the undergarments included four first interlocking fastening components in the form of loop fasteners 52 bonded to the moisture barrier 40 with a hot melt adhesive. The loop fasteners 52 comprised a tricot warp knit, brushed (napped) polyester yarn fabric purchased from Guilford Mills (No. 33517). A vinyl acetate copolymer sizing (RESYN 5904 from National Starch and Chemical Corp.) had been mist deposited on the back face of the loop material prior to heat treatment to obtain a final concentration of less than about 4 weight percent. The two loop fasteners 52 in the front waist region 30 measured 1.25 by 3.37 inches (3.18 by 8.56 cm) and were positioned to form an angle of about 33 degrees with the transverse axis. The two loop fasteners 52 in the back waist region 32 measured 1.5 by 2.0 inches (3.8 by 5.1 cm) and were aligned with the transverse axis 24 of the garment.

The Control A Straps included two elastic strap members 50 formed of an elastic material purchased from Shelby Elastics of Shelby, N.C., USA. The Control A Straps had a length of about 10.5 inches (26 cm.) and a width of about 1 inch (2.5 cm.). The strap ends were ultrasonically bonded to prevent raveling. The second interlocking fastening components were in the form of hook fasteners 54 bonded at the ends of the strap members 50. The hook material was purchased from Velcro USA and identified as No. HTH-840 including 22 Series hooks. The hook fasteners 54 measured 0.876 by 1.625 inches (2.23 by 4.13 cm) and had the unidirectional hooks pointing toward the center of the strap. Each hook fastener 54 had three rows of hooks at a free end ultrasonically deformed to form a grasping region 88. The hook fasteners 54 were ultrasonically bonded to the strap members 50. Ten of the hook fasteners of the Control A Straps were measured according to the bending index procedure set forth below and found to have an average bending index of $-0.098$ inch$^{-1}$ ($-0.039$ cm$^{-1}$) in the direction of the primary meridian 80. No measurement of bending index in the direction of the secondary meridian was made.

The Example A Straps were identical to the Control A Straps with the exception of the hook fasteners 54. The hook fasteners 54 of the Example A Straps were modified to have a concave configuration toward the first major surface 74. Each of these hook fasteners was heated to 308 degrees Fahrenheit (153° C.) and pressed against a mold surface for 5 seconds. The mold surface had the curvature of an approximately 3.25 inch (8.3 cm) diameter sphere. Ten of the hook fasteners of the Example A Straps were measured according to the bending index procedure set forth below and found to have an average bending index of 0.684 inch$^{-1}$ (0.269 cm$^{-1}$) in the direction of the primary meridian 80. No measurement of bending index in the direction of the secondary meridian was made.

This test used 10 male and 10 female participants. Each participant wore 16 undergarments with one pair of Example A Straps and 16 undergarments with one pair of Control A Straps. After donning each undergarment with a pair of strap members, each participant put on their clothing, walked about, and then sat in a chair, all in a span of less than about two minutes. Thereafter, each participant stood and pulled their clothing and the undergarment down to the knees and back up over the hips without unfastening the strap members. The lowering and raising cycle was repeated for a total of eight cycles for each undergarment. The undergarment was then removed and the complete procedure repeated with a new undergarment and the same strap members, until each pair of the strap members was tested with 16 undergarments.

An observer recorded information on the placement of the hook fastener on the loop fastener and the instances of pop-offs. The Example A Straps experienced 7 pop-offs and the Control A Straps experienced 20 pop-offs. The seven hook fasteners from the Example A Straps that resulted in the 7 pop-offs were analyzed and it was determined that only one of those hook fasteners retained a concave configuration.

Participants also wore the undergarments overnight with and without underclothing, but no significant differences between the Example A Straps and the Control A Straps was noted.

A bench test was conducted to evaluate various resilient interlocking fastening components 54 with different degrees of curvature. The test was designed to simulate use conditions in a laboratory environment without products being worn. With reference to FIGS. 10 and 11, an undergarment 20 and a strap member 50 were placed in an apparatus 130 with one hook fastener 54 of the strap member 50 engaged with one loop fastener 52 of the undergarment. The undergarment was the same as that described above in relation to the simulation test of the Example A Straps and the Control A Straps. In general, this test moved an elastic waistband of an underpant over the hook fastener 54 to simulate clothing being applied over the undergarment.

Again with reference to FIGS. 10 and 11, the test apparatus 130 included a frame 132, a formed block 134, a pair of paper clamps 136, and a pair of fasteners 138. The frame 132 comprised a wood structure having a length of 36 inches (91.4 cm), a width of 2.75 inches (7 cm), and a thickness of 0.75 inch (1.9 cm). The frame 132 can be secured to a workspace by clamps or other suitable means (not shown).

The formed block 134 was comprised of plaster of Paris and had one cast surface 140 which was shaped to approximate the female torso. The cast surface 140 was formed from a clay mold of the plastic mannequin 21 illustrated in FIG. 1, in the region where the loop fastener 52 of an undergarment 20 would be placed. The formed block 134 had a length of 3.5 inches (8.9 cm), a width of 3 inches (7.6 cm), and a varying thickness of about 1.5 inches (3.8 cm).

The block 134 was positioned on the frame 132 so that cast surface 140 was directed away from the frame and the length dimension of the block was aligned with the length dimension of the frame. The block 134 was oriented so that the corner of the undergarment which is positioned on the cast surface 140 approximates the shape that would be encountered if the undergarment were placed on the mannequin 21. The block 134 was located 11.5 inches (29.2 cm) from a first end of the frame 132 and 6.5 inches (16.5 cm) from the opposite second end of the frame. Glue or other suitable means can be used to bond the block 134 to the frame 132. A piece of hook material (not shown) was bonded to the cast surface 140 so that the hooks project upward from the block 134. This hook material prevents the undergarment 20 from sliding while testing.

The paper clamps 136 were mounted on the frame 132 by the fasteners 138. One of the clamps 136 was spaced 4.5 inches (11.4 cm) from the formed block 134 and the other clamp 136 was spaced 14.5 inches (36.8 cm) from the formed block. Suitable paper clamps 136 are 2 inches (5.1 cm) wide and available under the trade designation Binder Clips #10100 Large from GLL Corporation of Cadstadt, N.J. The fasteners 138 may comprise screws and washers as illustrated or other suitable means.

The strap members were evaluated by placing an undergarment 20 on the frame 132 so that the bodyside of the undergarment rested on the cast surface 140 of the formed block 134 and the opposite side of the undergarment was secured in the nearer of the two paper clamps 136. The undergarment 20 was positioned so that the bodyside liner 44 of the undergarment 20 was disposed toward the cast surface 140 and a loop fastener 52 was directly over the cast surface 140. The spacing of the paper clamps 136 may need to be adjusted for different size garments. To test a diaper or fitted brief type product, one approach is to position one product in one clamp and an identical product in the other clamp.

For each strap member 50 that was tested, a hook fastener 54 from the strap member 50 was placed on the loop fastener 52 that was positioned over the cast surface 0 140. The interlocking fastening components 52 and 54 were pressed together. The elastic strap member 50 was stretched to approximately 2 pounds (907 grams) of force and clamped in that extended condition in the other paper clamp 136.

To simulate use conditions, the hook fastener 54 was disengaged from the loop fastener 52 by pulling on the grasping region 88 (FIG. 3) or distal end of the hook fastener. The hook fastener 54 was then reattached to the loop fastener 52. This disengagement and reattachment cycle was repeated two more times, for a total of three cycles.

The waistband region of a pair of underpants was moved back and forth across the hook fastener 54 ten times or until a pop-off occurred. As used herein, a pop-off means that the hook fastener 54 comes loose from the loop fastener 52. Suitable underpants for use in the present test include ladies briefs size 6 cotton underwear identified under the tradename FRUIT OF THE LOOM by Fruit of the Loom, Inc. of Chicago, Ill., or similarly constructed underpants.

The tester grasped the elastic waistband of the underpants at two locations about four inches apart. The tester elongated the waistband by approximately 50 percent to a length between the two locations of about six inches. The waistband was placed on the undergarment 20 with the waistband making an angle of about 45 degrees with the length dimension of the strop member 50, when viewed from above. In the height dimension, the hands of the tester were positioned about even with the top surface of the frame 132. The hands of the tester were then moved horizontally back and forth in a direction that is perpendicular to the length dimension of the strap member 50, so that the waistband of the underpants was moved onto and then off the hook fastener 54.

This movement of the underpants over the undergarment 20 and the hook fastener 54 was designed to simulate applying and removing underwear during use of the undergarment 20.

Each movement of the waistband of the underpants onto and then off the hook fastener 54 was considered one cycle. This movement was repeated until a pop-off occurred, to a maximum of ten cycles. The tester recorded whether a pop-off occurred and the number of the cycle during which the pop-off occurred, if any. For each strap member 50 that was tested, a new loop fastener 52 was also used to ensure that the loop material did not wear out.

Ten Control A Straps and ten Example A Straps as described above in relation to the simulation test were also evaluated in the foregoing bench test. The results of the bench test are reported in Table 1 below.

TABLE 1

| Strap | Control A Strap | | Example A Strap | |
|---|---|---|---|---|
| No. | Cycle | Pop-Off | Cycle | Pop-Off |
| 1 | 1 | yes | 10 | no |
| 2 | 2 | yes | 10 | no |
| 3 | 1 | yes | 10 | no |
| 4 | 1 | yes | 10 | no |
| 5 | 1 | yes | 4 | yes |
| 6 | 1 | yes | 10 | no |
| 7 | 1 | yes | 10 | no |
| 8 | 3 | yes | 10 | no |
| 9 | 3 | yes | 10 | no |
| 10 | 1 | yes | 10 | no |
| Avg. | 1.5 | 100% | 9.4 | 10% |

A summary relating to the Control A Straps and the Example A Straps, including bending index values and bench test results, is reported in Table 2 below.

TABLE 2

| Sample | Bending Index Primary Meridian (inch$^{-1}$) | Bending Index Secondary Meridian (inch$^{-1}$) | Percent Pop Offs | Avg. Cycles |
|---|---|---|---|---|
| Control A Strap | −0.098 | — | 100 | 1.5 |
| Ex. A1 Strap | 0.684 | — | 10 | 9.4 |

A further bench test was performed using straps identified as Control B Straps and Example Straps B1, B2 and B3. Each of these straps is described below.

The Control B Straps included second interlocking fastening components 54 that comprised a backing structure 72 formed of a polypropylene resin available from Ferro Corporation of Cleveland, Ohio, under the trade designation PF-7823, and having an average thickness of about 0.2 millimeters (8 mil). The average bending index of the second interlocking fastening components 54 was determined to be −0.019 inch$^{-1}$ (−0.007 cm$^{-1}$) in the direction of the primary meridian 80. The bending index was based on an examination of 6 images of the side edges 84 of 6 second interlocking fastening components 54. No measurement of bending index in the direction of the secondary meridian was made.

The Example B1 Straps included second interlocking fastening components 54 that comprised a backing structure 72 formed of the PF-7823 polypropylene resin available from Ferro Corporation and having an average thickness of about 0.2 millimeters (8 mil). The average bending index of the second interlocking fastening components 54 was determined to be 0.316 inch$^{-1}$ (0.124 cm$^{-1}$) in the direction of the primary meridian 80 and 0.163 inch$^{-1}$ (0.064 cm$^{-1}$) in the direction of the secondary meridian. The bending index was based on an examination of 8 images of the side and end edges 84 and 86 of 8 second interlocking fastening components 54.

The Example B2 Straps included second interlocking fastening components 54 that comprised a backing structure 72 formed of the PF-7823 polypropylene resin available from Ferro Corporation and having an average thickness of about 0.2 millimeters (8 mil). The average bending index of the second interlocking fastening components 54 was determined to be 0.52 inch$^{-1}$ (0.205 cm$^{-1}$) in the direction of the primary meridian 80 and 0.304 inch$^{-1}$ (0.120 cm$^{-1}$) in the direction of the secondary meridian. In calculating the bending index in the direction of the secondary meridian, one remote data point was not included. Thus, the bending index in the direction of the primary meridian was based on an examination of 9 images of the side edges 84 of 9 second interlocking fastening components 54, and the bending index in the direction of the secondary meridian was based on an examination of 8 images of the end edges 86 of 8 second interlocking fastening components.

The Example B3 Straps included second interlocking fastening components 54 that comprised a backing structure 72 formed of the PF-7823 polypropylene resin available from Ferro Corporation and having an average thickness of about 0.2 millimeters (8 mil). The average bending index of the second interlocking fastening components 54 was determined to be 0.649 inch$^{-1}$ (0.256 cm$^{-1}$) in the direction of the primary meridian 80 and 1.08 inch$^{-1}$ (0.425 cm$^{-1}$) in the direction of the secondary meridian. In calculating the bending index in the direction of the secondary meridian, one remote data point was not included. Thus, the bending index in the direction of the primary meridian was based on an examination of 10 images of the side edges 84 of 10 second interlocking fastening components 54, and the bending index in the direction of the secondary meridian was based on an examination of 9 images of the end edges 86 of 9 second interlocking fastening components.

The second interlocking fastening components 54 of Example Straps B1, B2 and B3 were made by contact with a heated block having a particular depression to receive the backing structure 72 of the fastening component. A plaster of Paris mold of the depression of each of the blocks was made and the bending index of the mold surface was measured. The mold of the depression used to make the Example B1 Straps had a bending index of 0.43 inch$^{-1}$ (0.169 cm$^{-1}$) in the direction of the fastener's primary meridian and 0.29 inch$^{-1}$ (0.114 cm$^{-1}$) in the direction of the fastener's secondary meridian. The mold of the depression used to make the Example B2 Straps had a bending index of 0.59 inch$^{-1}$ (0.232 cm$^{-1}$) in the direction of the fastener's primary meridian and 0.57 inch$^{-1}$ (0.224 cm$^{-1}$) in the direction of the fastener's secondary meridian. The mold of the depression used to make the Example B3 Straps had a bending index of 0.61 inch$^{-1}$ (0.24 cm$^{-1}$) in the direction of the fastener's primary meridian and 0.58 inch$^{-1}$ (0.228 cm$^{-1}$) in the direction of the fastener's secondary meridian.

The bench test results relating to the Control B Straps and the Example Straps B1, B2 and B3 are reported in Table 3 below. The test of the Example B1 Straps was interrupted after 8 straps had been tested.

TABLE 3

| Strap No. | Control B Strap Cycle | Pop-Off | Ex. B1 Strap Cycle | Pop-Off | Ex. B2 Strap Cycle | Pop-Off | Ex. B3 Strap Cycle | Pop-Off |
|---|---|---|---|---|---|---|---|---|
| 1 | 1 | yes | 3 | yes | 4 | yes | 10 | no |
| 2 | 3 | yes | 2 | yes | 10 | no | 10 | no |
| 3 | 2 | yes | 2 | yes | 10 | no | 10 | no |
| 4 | 1 | yes | 10 | no | 10 | no | 10 | no |
| 5 | 1 | yes | 3 | yes | 10 | no | 10 | no |
| 6 | 1 | yes | 2 | yes | 10 | no | 10 | no |
| 7 | 2 | yes | 2 | yes | 10 | no | 10 | no |
| 8 | 2 | yes | 3 | yes | 5 | yes | 10 | no |
| 9 | 2 | yes | | n/a | 5 | yes | 10 | no |
| 10 | 6 | yes | | n/a | 10 | no | 10 | no |
| Avg. | 2.1 | 100% | 3.4 | 88% | 8.4 | 30% | 10 | 0% |

A summary relating to the Control B Straps and the Example Straps B1, B2 and B3, including bending index values and bench test results, is reported in Table 4 below.

TABLE 4

| Sample | Bending Index Primary Meridian (inch$^{-1}$) | Bending Index Secondary Meridian (inch$^{-1}$) | Percent Pop Offs | Avg. Cycles |
|---|---|---|---|---|
| Control B Strap | −0.019 | — | 100 | 2.1 |
| Ex. B1 Strap | 0.316 | 0.163 | 88 | 3.4 |
| Ex. B2 Strap | 0.520 | 0.304 | 30 | 8.4 |
| Ex. B3 Strap | 0.649 | 1.080 | 0 | 10.0 |

A shape retention test was developed to evaluate the ability of a second interlocking fastening component 54 to maintain a concave configuration during simulated use conditions. The test utilized an undergarment 20 of the type described above in relation to the test of Control A Straps, the apparatus 130 illustrated in FIGS. 10 and 11, and various strap members 50.

For each test of a particular type of strap member 50, the bending index of a second interlocking fastening component 54 of the strap member 50 is determined and recorded. Then, an undergarment 20 is positioned on the apparatus 130 as described in the above bench test, and the strap members are attached to the first interlocking fastening components 52. The second interlocking fastening component 54 for which the bending index was determined is then detached from the first interlocking fastening component 52 by pulling on the grasping region 88 or distal end of the second fastening component. This attachment and detachment of the second interlocking fastening component 54 for which the bending index was measured from a first interlocking fastening component 52 constitutes a single attachment and detachment cycle. This cycle is repeated for a total of 15 cycles. After 15 cycles, the bending index of the same second interlocking fastening component 54 is again determined and recorded.

The strap members 50 that were evaluated by the shape retention test were designated Control C Straps, Example Straps C1 and C2, Control D Straps, and Example Straps D1, D2 and D3. Each of these strap members 50 is described below.

The Control C Straps included second interlocking fastening components 54 that comprised a backing structure 72 formed of the PF-7823 polypropylene resin available from Ferro Corporation and having an average thickness of about 0.2 millimeters (8 mil). The average bending index of 6 of the second interlocking fastening components 54 was determined before the 15 attachment and detachment cycles to be 0.766 inch$^{-1}$ (0.302 cm$^{-1}$), based on an examination of 6 photocopy images of the side edges 84 of the 6 second interlocking fastening components 54. The average bending index of the same 6 fastening components 54 was determined after the 15 attachment and detachment cycles to be 0.633 inch$^{-1}$ (0.249 cm$^{-1}$), based again on an examination of 6 photocopy images of the side edges 84 of the 6 second interlocking fastening components 54.

The Example C1 Straps included second interlocking fastening components 54 that comprised a backing structure 72 formed of the PF-7823 polypropylene resin available from Ferro Corporation and having an average thickness of 0.168 millimeters (6.7 mil). The average bending index of 6 of the second interlocking fastening components 54 was determined before the 15 attachment and detachment cycles to be 0.420 inch$^{-1}$ (0.165 cm$^{-1}$), based on an examination of 6 photocopy images of the side edges 84 of the 6 second interlocking fastening components 54. The average bending index of the same 6 fastening components 54 was determined after the 15 attachment and detachment cycles to be 0.086 inch$^{-1}$ (0.034 cm$^{-1}$), based again on an examination of 6 photocopy images of the side edges 84 of the 6 second interlocking fastening components 54. The average bending index of 0.086 inch$^{-1}$ included 2 negative values, indicating instances of a convex shape after testing.

The Example C2 Straps included second interlocking fastening components 54 that comprised a backing structure 72 formed of the PF-7823 polypropylene resin available from Ferro Corporation and having an average thickness of 0.135 millimeters (5.3 mil). The average bending index of 6 of the second interlocking fastening components 54 was determined before the 15 attachment and detachment cycles to be 0.370 inch$^{-1}$ (0.146 cm$^{-1}$), based on an examination of 6 photocopy images of the side edges 84 of the 6 second interlocking fastening components 54. The average bending index of the same 6 fastening components 54 was determined after the 15 attachment and detachment cycles to be 0.393 inch$^{-1}$ (0.153 cm$^{-1}$), based again on an examination of 6 photocopy images of the side edges 84 of the 6 second interlocking fastening components 54. The average bending index of 0.393 inch$^{-1}$ included 1 negative value, indicating an instance of a convex shape after testing.

The Control D Straps included second interlocking fastening components 54 that comprised a backing structure 72 formed of the PF-7823 polypropylene resin available from Ferro Corporation and having an average thickness of 0.198 millimeters (7.8 mil). The average bending index of 10 of the second interlocking fastening components 54 was determined before the 15 attachment and detachment cycles to be 0.597 inch$^{-1}$ (0.235 cm$^{-1}$), based on an examination of 10 photocopy images of the side edges 84 of the 10 second interlocking fastening components 54. The average bending index of the same 10 fastening components 54 was determined after the 15 attachment and detachment cycles to be 0.497 inch$^{-1}$ (0.196 cm$^{-1}$), based again on an examination of 10 photocopy images of the side edges 84 of the 10 second interlocking fastening components 54.

The Example D1 Straps included second interlocking fastening components 54 that comprised a backing structure 72 formed of the PF-7823 polypropylene resin available from Ferro Corporation and having an average thickness of 0.414 millimeters (16.3 mil). The average bending index of 10 of the second interlocking fastening components 54 was determined before the 15 attachment and detachment cycles to be 0.405 inch$^{-1}$ (0.159 cm$^{-1}$), based on an examination of 10 photocopy images of the side edges 84 of the 10 second interlocking fastening components 54. The average bending index of the same 10 fastening components 54 was determined after the 15 attachment and detachment cycles to be 0.325 inch$^{-1}$ (0.128 cm$^{-1}$), based again on an examination of 10 photocopy images of the side edges 84 of the 10 second interlocking fastening components 54.

The Example D2 Straps included second interlocking fastening components 54 that comprised a backing structure 72 formed of the PF-7823 polypropylene resin available from Ferro Corporation and having an average thickness of 0.495 millimeters (19.5 mil). The average bending index of 10 of the second interlocking fastening components 54 was determined before the 15 attachment and detachment cycles to be 0.453 inch$^{-1}$ (0.178 cm$^{-1}$), based on an examination of 10 photocopy images of the side edges 84 of the 10 second interlocking fastening components 54. The average bending index of 9 of these 10 fastening components 54 was determined after the 15 attachment and detachment cycles to be 0.434 inch$^{-1}$ (0.017 cm$^{-1}$), based again on an examination of 9 photocopy images of the side edges 84 of the 9 second interlocking fastening components 54.

The Example D3 Straps included second interlocking fastening components 54 that comprised a backing structure 72 formed of the PF-7823 polypropylene resin available from Ferro Corporation and having an average thickness of 0.340 millimeters (13.4 mil). The average bending index of 10 of the second interlocking fastening components 54 was determined before the 15 attachment and detachment cycles to be 0.554 inch$^{-1}$ (0.218 cm$^{-1}$), based on an examination of 10 photocopy images of the side edges 84 of the 10 second interlocking fastening components 54. The average bending index of the same 10 fastening components 54 was determined after the 15 attachment and detachment cycles to be 0.371 inch$^{-1}$ (0.146 cm$^{-1}$), based again on an examination of 10 photocopy images of the side edges 84 of the 10 second interlocking fastening components 54.

A stiffness test was also used to determine the degree of stiffness of the second interlocking fastening components 54 of several of the Control and Example Straps. In particular, the stiffness of a backing structure 72 of a second interlocking fastening component 54 was determined using a Gurley stiffness test. The test measured the stiffness of a particular backing material prior to the material being imparted with any concave curvature. The stiffness values of the tested strap members are shown in Table 5 below. The stiffness values are averages reported in milligrams based on the indicated number of samples.

TABLE 5

| Sample | Number | Gurley Stiffness |
| --- | --- | --- |
| Control C Strap | 15 | 860 |
| Ex. C1 Strap | 15 | 708 |
| Ex. C2 Strap | 15 | 263 |
| Control D Strap | 15 | 696 |
| Ex. D1 Strap | 15 | 4649 |
| Ex. D2 Strap | 15 | 7159 |
| Ex. D3 Strap | 15 | 3043 |

A suitable technique for determining Gudey stiffness is set forth in TAPPI T543 PM-83. For purposes of the present invention, the dimensions of the sample employed for determining Gurley stiffness measured 1 inch (2.54 cm) in length and 0.5 inch (1.27 cm) in width.

The bending index of a resilient interlocking fastening component 54 may be determined using the following bending index procedure. The procedure utilizes an Image Analysis System that is available under the trade designation QUANTIMET 970 with QUIPS Version 8.00 software from Leica/Cambridge Instruments of 111 Deer Lake Road, Deerfield, Ill., USA. Other equipment used to determine the bending index of a specimen includes a video camera with a 50 mm EI-Nikkor lens at f/2.8; a 5 mm extension-tube; a black scanning electron microscope vice or other suitable clamps; a black photodrape cloth; an 8-bulb octagonal ring illuminator or several flood lamps; incident darkfield lighting; a KREONITE macroviewer available from J. Kelly Corp., of Darien, Ill., to support the camera, lens and illuminator; and white correction fluid, for example one available under the tradename LIQUID PAPER from The Gillette Company of Boston, Mass., used to highlight edge views, if needed. These components are placed to provide a vertical optical alignment.

In general, the strap member 50 is positioned in the scanning electron microscope vice so that the second interlocking fastening component 54 projects beyond the vice. The vice and strap member 50 are positioned above the photodrape cloth, and the fastening component is illuminated by the ring illuminator. The lens of the video camera is adjusted to provide an image of the fastening component, either at an edge of the backing structure 72, which generally provides the clearest image, or at a location inward of an edge. The image is input to the image analysis system and the control software program is initiated. When the backing curvature is observed to be convex, a negative backing number ("BACKNUM") is entered when prompted, meaning that the measured radius and bending index are negative values.

One suitable software routine for controlling the image analysis system to measure the bending index of an interlocking fastening component 54 is set forth below:

```
COND = 50 MM EL-NIKKOR; F/2.8, 5MM X-TUBE; 8-BULB
   OCTAGONAL RING ILLUMIN; INCIDENT DARKFIELD;
   BLACK BCKGND SEM VICE PAINTED BLACK; VERTICAL
   ALIGN OF HOOK PLASTIC
Enter specimen identity
Scanner (No. 1 Chalnicon LV=0.00 SENS=1.66 PAUSE)
Calibrate User Specified (Cal Value = 0.001855 inches per pixel)
Load Shading Corrector (pattern - CTUBE)
SUBRTN STANDARD
TEMP :=0
BACKNUM :=0.
Print" "
Print "RADIUS VALUES ARE IN INCHES"
Print" "
For FIELD
   Pause Message
   PLEASE ENTER BACKING NUMBER
   Input BACKNUM
   Pause
   Detect2D(Darker than 0, Delin)
   Pause Message
   PLEASE MOVE AND ALIGN FRAME . . .
   Image Frame (Pause) is Rectangle (X: 360, Y: 61, W: 129, H: 596.)
   Live Frame is Standard Live Frame
   Detect2D(Lighter than 31, Delin PAUSE)
   Amend (CLOSE by 10)
   Amend (SKELETON - by 50)
   Amend (SKELETON - Peel Ends by 125)
   Pseudo-Colour Transfer - LUT GREY, Full resolution, Full frame
   Edit (pause)
```

| Measure feature | AREA | PERIMETER | FERET 0 | FERET 90 |
|---|---|---|---|---|
| | X.MAX | X.FCP | Y.FCP | LENGTH |
| | BREADTH | | | |

```
   using 56 ferets
     into array FEATURE (of 200 features and 20 parameters)
Accept FEATURE FERET from 0.10000 to 1000.
FEATURE CALC.A := AREA/FERET90
FEATURE CALC.B := BREADTH - CALC.A
FEATURE CALC := (CALC.B/2.) + ((FERET90 * FERET90)/
     (8. *CALC.B))
FEATURE CALC.C := CALC + CALC.A/2.
FEATURE SHAPE := 1./CALC.C
FEATURE FERET 0 := FERETO/CAL.CONST
Print FEATURE "BACKING RADIUS=", CALC.C, "BENDING
INDEX=",
     SHAPE, "BACKING#=", BACKNUM
Accept all features in FEATURE
Pause Message
PLEASE SELECT ANOTHER BACKING, OR FINISH
Pause
Next FIELD
Pause Message
PLEASE DO A 'FORM FEED' ON PRINTER!
Pause
For LOOPCOUNT = 1 to 5
Print " "
Next
END OF PROGRAM
```

One skilled in the art will recognize that appropriate adjustments for lighting and positioning would be individual to any particular optical input system.

As an alternative approach, the bending index of a second interlocking fastening component 54 measured at an edge 84 or 86 of the backing structure 72 may be determined from a photocopy of the fastening component. In particular, the second interlocking fastening component 54 may be positioned on edge on a photocopy machine and copied. The resulting image can be analyzed in the image analysis system described above to determine the bending index at the edge of the fastening component. Further, the bending index of other structures, such as plaster of Paris casts of forming molds used to make the second interlocking fastening components 54, may also be analyzed using this image analysis system.

The foregoing detailed description has been for the purpose of illustration. Thus, a number of modifications and changes may be made without departing from the spirit and scope of the present invention. For instance, alternative or optional features described as part of one embodiment can be used to yield another embodiment. Additionally, two named components could represent portions of the same structure. Therefore, the invention should not be limited by the specific embodiments described, but only by the claims.

We claim:

1. An absorbent article for use by a wearer, comprising:
   a garment having a first waist region, a second waist region, and a crotch region positioned between and interconnecting the first and second waist regions, the garment comprising a first interlocking fastening component disposed in the first waist region, the first interlocking fastening component comprising a plurality of engaging elements; and
   at least one strap member for securing the garment about the wearer, the strap member having opposite first and second end portions and comprising:
      a second interlocking fastening component bonded to the first end portion, the second interlocking fastening component adapted for refastenable attachment to the first interlocking fastening component and comprising:
      a backing structure formed of a resilient material and having a concave major surface with a bending index of at least about 0.3 inch $^{-1}$ when the second interlocking fastening component is in an unfastened, relaxed state; and
      a plurality of engaging elements projecting from the major surface, the engaging elements of the first and second interlocking fastening components comprising self-engaging shaped geometric materials; and
   means for attaching the second end portion to the second waist region.

2. The absorbent article of claim 1, wherein the backing structure is adapted to retain a bending index of at least about 0.3 inch when the second interlocking fastening component is in an unfastened, relaxed state after 15 attachment and detachment cycles of the first and second interlocking fastening components.

3. The absorbent article of claim 1, wherein:
   the strap member has a width dimension and a length dimension greater than the width dimension;
   the second interlocking fastening component has a primary meridian generally parallel to the length dimension of the strap member and a secondary meridian which intersects the primary reeddian at a 90 degree angle; and
   the concavity is in the direction of the primary meridian.

4. The absorbent article of claim 1, wherein:
   the strap member has a width dimension and a length dimension greater than the width dimension;
   the second interlocking fastening component has a primary meridian generally parallel to the length dimension of the strap member and a secondary meridian which intersects the primary meridian at a 90 degree angle; and
   the concavity is in the direction of the secondary meridian.

5. The absorbent article of claim 1, wherein the first major surface is three-dimensionally concave.

6. The absorbent article of claim 1, wherein the first interlocking fastening component comprises a flexible fabric.

7. The absorbent article of claim 6, wherein the first interlocking fastening component comprises a loop material and the second interlocking fastening component comprises a hook material.

8. The absorbent article of claim 1, wherein the bending index is at least about 0.5 inch $^{-1}$ when the second interlocking fastening component is in an unfastened, relaxed state.

9. The absorbent article of claim 1, wherein the bending index is from about 0.5 to about 1.1 inch $^{-1}$ when the second interlocking fastening component is in an unfastened, relaxed state.

10. The absorbent article of claim 1, wherein the bending index in the direction of a primary meridian is at least about 0.6 inch $^{-1}$ when the second interlocking fastening component is in an unfastened, relaxed state and the bending index in the direction of a secondary meridian is at least about 1 inch $^{-1}$ when the second interlocking fastening component is in an unfastened, relaxed state.

11. The absorbent article of claim 1, wherein the second interlocking fastening component has a Gurley stiffness of about 250 to about 3000 milligrams.

12. An absorbent article for use by a wearer, comprising:
   a garment having a first waist region, a second waist region, and a crotch region positioned between and interconnecting the first and second waist regions, the garment comprising a first interlocking fastening component disposed in the first waist region, the first interlocking fastening component comprising a plurality of engaging elements; and at least one strap member for securing the garment about the wearer, the strap member having opposite first and second end portions and comprising:
- a second interlocking fastening component bonded to the first end portion, the second interlocking fastening component adapted for refastenable attachment to the first interlocking fastening component and comprising:
  - a backing structure formed of a resilient material and having a concave major surface when the second interlocking fastening component is in an unfastened, relaxed state, the major surface having a central portion that is elevated by at least about 1.0 millimeter from a plane containing opposite peripheral points when the second interlocking fastening component is in an unfastened, relaxed state; and
  - a plurality of engaging elements projecting from the major surface, the engaging elements of the first and second interlocking fastening components comprising self-engaging shaped geometric materials; and means for attaching the second end portion to the second waist region.

13. The absorbent article of claim 12, wherein:

the major surface has opposite side edges and opposite end edges; and the central portion is elevated by at least about 1.0 millimeter from a plane containing the opposite end edges when the second interlocking fastening component is in an unfastened, relaxed state.

14. The absorbent article of claim 12, wherein:

the major surface has opposite side edges and opposite end edges; and the central portion is elevated by at least about 1.0 millimeter from a plane containing the opposite side edges when the second interlocking fastening component is in an unfastened, relaxed state.

15. The absorbent article of claim 12, wherein the central portion is elevated by at least about 1.5 millimeters from a plane containing opposite peripheral points when the second interlocking fastening component is in an unfastened, relaxed state.

16. The absorbent article of claim 15, wherein the central portion is elevated by about 1.5 to about 2.0 millimeters from a plane containing opposite peripheral points when the second interlocking fastening component is in an unfastened, relaxed state.

17. The absorbent article of claim 12, wherein the backing structure is adapted to retain the central portion at an elevation of at least about 1.0 millimeters when the second interlocking fastening component is in an unfastened, relaxed state after 15 attachment and detachment cycles of first and second interlocking fastening components.

18. An absorbent article for use by a wearer, comprising:

a garment having a first waist region, a second waist region, and a crotch region positioned between and interconnecting the first and second waist regions, the garment comprising at least one first interlocking fastening component disposed in each of the waist regions, the first interlocking fastening component comprising a plurality of engaging elements; and a pair of strap members for securing the garment about the wearer, each strap member having opposite first and second end portions and comprising a second interlocking fastening component bonded to each end portion, each second interlocking fastening component adapted for refastenable attachment to the at least one first interlocking fastening component and comprising:
- a backing structure formed of a resilient material and having a concave major surface with a bending index of at least about 0.3 inch $^{-1}$ when the second interlocking fastening component is in an unfastened, relaxed state; and
- a plurality of engaging elements projecting from the major surface the engaging elements of the first and second interlocking fastening components comprising self-engaging shaped materials.

* * * * *